United States Patent
Dole et al.

(10) Patent No.: US 8,778,656 B2
(45) Date of Patent: Jul. 15, 2014

(54) ORGANIC ACID PRODUCTION IN MICROORGANISMS BY COMBINED REDUCTIVE AND OXIDATIVE TRICABOXYLIC ACID CYLCE PATHWAYS

(75) Inventors: Sudhanshu Dole, North Andover, MA (US); R. Rogers Yocum, Lexington, MA (US)

(73) Assignee: Myriant Corporation, Quincy, MA (US)

(*) Notice: Subject to any disclaimer, the term of this patent is extended or adjusted under 35 U.S.C. 154(b) by 0 days.

(21) Appl. No.: 13/508,095

(22) PCT Filed: Nov. 18, 2010

(86) PCT No.: PCT/US2010/057291
§ 371 (c)(1), (2), (4) Date: May 4, 2012

(87) PCT Pub. No.: WO2011/063157
PCT Pub. Date: May 26, 2011

(65) Prior Publication Data
US 2012/0225461 A1    Sep. 6, 2012

Related U.S. Application Data

(60) Provisional application No. 61/281,486, filed on Nov. 18, 2009.

(51) Int. Cl.
*C12N 1/20* (2006.01)

(52) U.S. Cl.
USPC .................................................. 435/252.33

(58) Field of Classification Search
None
See application file for complete search history.

(56) References Cited

U.S. PATENT DOCUMENTS

| | | |
|---|---|---|
| 6,455,284 B1 | 9/2002 | Gokarn et al. |
| 7,223,567 B2 | 5/2007 | Ka-Yiu et al. |
| 7,244,610 B2 | 7/2007 | Ka-Yiu et al. |
| 7,262,046 B2 | 8/2007 | Ka-Yiu et al. |
| 7,629,162 B2 | 12/2009 | Zhou et al. |
| 7,790,416 B2 | 9/2010 | Ka-Yiu et al. |
| 2006/0073577 A1 | 4/2006 | Ka-Yiu et al. |
| 2007/0015261 A1 | 1/2007 | D'elia et al. |
| 2009/0148914 A1 | 6/2009 | Causey et al. |

FOREIGN PATENT DOCUMENTS

| | | |
|---|---|---|
| WO | 2008115958 A2 | 9/2008 |
| WO | 2009065777 A1 | 5/2009 |
| WO | 2010115067 A2 | 10/2010 |

OTHER PUBLICATIONS

Causey, T. B. et al. "Engineering *Escherichia coli* for efficient conversion of glucose to pyruvate" Proceedings of National Academy of Sciences USA, 2004, pp. 2235-2240, vol. 101.

Cronan, J. and Laporte, D. "Tricarboxylic acid cycle and glyoxylate bypass" in "*Escherichia coli* and Salmonella Cellular and Molecular Biology." editors Neidhardt, F. et al. 1996, pp. 206-215, vol. 1, ASM Press, Washington, DC., USA.

Datsenke, K. A. and Wanner, B. L. "One-step inactivation of chromosomal genes in *Escherichia coli* K-12 using PCR products" Proceedings of National Academy of Sciences USA, 2000, pp. 6640-6645, vol. 97.

Deutscher, J., et al. "How phosphotransferase system-related protein phosphorylation regulates carbohydrate metabolism in bacteria." Microbiology and Molecular Biology Review, 2006, pp. 70:939-1031, vol. 70.

Jansen, M. et al. "Breakthrough technology for fermentative succinic acid production" Poster C25, Metabolic Engineering VIII, 2010, Engineering Conferences International, 32 Broadway, Suite 314, New York, NY 10004, USA.

Jantama, K. et al. "Combining metabolic engineering and metabolic evolutions to develop nonrecombinant strains of *Escherichia coli* C that produce succinate and malate." Biotechnology and Bioengineering, 2008, pp. 1140-1153, vol. 99.

Jantama, K. et al. "Eliminating side products and increasing succinate yields in engineered strains of *Escherichia coli* C" Biotechnology Bioengineering, 2008, pp. 881-893, vol. 101.

Kanai, T. et al. "A regulatory factor Fil1p,involved in derepression of the isocitrate lyase gene in *Saccharomyces cerevisiae*—a possible mitochondrial protein necessary for protein synthesis in mitochondria." European Journal of Biochemistry, 1998, pp. 212-220, vol. 256.

Lee, S.J. et al. "Metabolic Engineering of *Escherichia coli* for enhanced production of succinic acid, based on genome comparison and in silico gene knockout stimulation." Applied and Environmental Microbiology, 2005, pp. 7880-7887, vol. 71.

Lin, H. et al. "Metabolic engineering of aerobic succinate production systems in *Escherichia coli* to improve process productivity and achieve the maximum theoretical succinate yield." Metabolic Engineering, 2005, pp. 116-127, vol. 7.

Lin, H. et al. "Genetic reconstruction of the aerobic central metabolism in *Escherichia coli* for the absolute aerobic production of succinate." Biotechnology and Bioengineering, 2005, pp. 148-156, vol. 89.

Martinez, I. et al. "Metabolic impact of the level of aeration during cell growth on anaerobic succinate production by an engineered *E. coli* strain." Metabolic Engineering, 2010, 499-509, vol. 12.

Sanchez, A. M. et al. "Novel pathway engineering design of the anaerobic central metabolic pathway in *Escherichia coli* to increase succinate yield and productivity." Metabolic Engineering, 2005, pp. 229-239, vol. 7.

(Continued)

Primary Examiner — Nashaat Nashed
(74) Attorney, Agent, or Firm — Ramasamy Mannan

(57) ABSTRACT

This invention relates to succinic acid production from renewable feedstock using microbial biocatalysts genetically modified to produce succinic acid in commercially significant quantities. More specifically, this invention relates to the genetic manipulations in the pathway of carbon from renewable feedstock to succinic acid.

19 Claims, 4 Drawing Sheets

(56) References Cited

OTHER PUBLICATIONS

Silhavy, T. et al. "Procedure 10—Preparation of P1vir Lysates" in "Experiments With Gene Fusions" 1984 pp. 107-112, Cold Spring Harbor Laboratory Press, Cold Spring Harbor, NY.

Vemuri, G. N. et al. "Effects of growth mode and pyruvate carboxylase on succinic acid production by metabolically engineered strains of *Escherichia coli*." Applied and Environmental Microbiology, 2002, pp. 1715-1727, vol. 68.

Vemuri, G. N. et al. "Succinate production in dual-phase *Escherichia coli* fermentations depends on the time of transition from aerobic conditions." Journal of Industrial and Microbiological Biotechnology, 2002, pp. 325-332, vol. 28.

Vemuri, G. N. et al. "Overflow metabolism in *Escherichia coli* during steady-state growth transcriptional regulation and effect of the redox ratio." Applied and Environmental Microbiology, 2006, pp. 3653-3661, vol. 72.

Vemuri, G. N. et al. "Increasing NADH oxidation reduces overflow metabolism in *Saccharomyces cerevisiae*." Proceedings of National Academy of Sciences USA, 2007, pp. 2402-2407, vol. 104.

Wang, Q. et al., (2006) "Genome scale in silico aided metabolic analysis and flux comparisons of *E. coli* to improve succinate production." Applied Microbiology and Biotechnology, 2006, pp. 887-894, vol. 73.

Wu, H. et al. "Improved succinic acid production in the anaerobic culture of an *Escherichia coli* pflB IdhA double mutant as a result of enhanced anapleurotic activities in the preceding aerobic culture" Applied and Environmental Microbiology, 2007, pp. 7837-7843, vol. 73.

Zhang, X. et al. "Metabolic evolution of energy-conserving pathways for succinate production in *Escherichia coli*." Proceedings of National Academy of Sciences USA, 2009, pp. 20180-20185, vol. 106.

Glucose to Succinate, Reductive Pathway:

$C_6 + NADH + FADH + 2\ CO_2 \longrightarrow 2\ Succ + 2\ ATP + NAD + FAD$

Glucose to Succinate, Glyoxylate Pathway:

$C_6 + 5\ NAD \longrightarrow 1\ Succ + 2\ ATP + 5\ NADH + 2\ CO_2$

Glucose to Succinate, Oxidative TCA Pathway:

$C_6 + 4\ NAD + 1\ NADP \longrightarrow 1\ Succ + 4\ ATP^{**} + 4\ NADH + 1\ NADPH + 2\ CO_2$ Balanced for Redox (NADH = FADH*):  5 x Reductive + 2 x Glyoxylate:

$7\ C_6 + 6\ CO_2 \longrightarrow 12\ Succ + 14\ ATP$  (Need 6 $K_2CO_3$ + 12 KOH)

Balanced for Redox (NADH = NADPH = FADH*):  5 x Reductive + 2 x Oxidative TCA:

$7\ C_6 + 6\ CO_2 \longrightarrow 12\ Succ + 18\ ATP$  (Need 6 $K_2CO_3$ + 12 KOH)

\* Reducing equivalents in the form of NADH, NADPH, and FADH are assumed to be interchangeable by transhydrogenase or the equivalent.

\*\* In some organisms, GTP is produced by the oxidative TCA cycle instead of ATP, but here it is assumed that they are energetically equivalent.

Figure 4

SEQUENCE LISTING

```
<160> NUMBER OF SEQ ID NOS: 9

<210> SEQ ID NO 1
<211> LENGTH: 70
<212> TYPE: DNA
<213> ORGANISM: Artificial Sequence
<220> FEATURE:
<223> OTHER INFORMATION: SYynthetic PCR Primer SD131

<400> SEQUENCE: 1
ttcctgaccc tgccaggcta ccgcctgtta gcgtaaacca ccacataact tgtgacggaa      60
gatcacttcg                                                            70

<210> SEQ ID NO 2
<211> LENGTH: 104
<212> TYPE: DNA
<213> ORGANISM: Artificial Sequence
<220> FEATURE:
<223> OTHER INFORMATION: Synthetic PCR Primer SD132

<400> SEQUENCE: 2
tgcggcgtga acgccttatc cggcctacag tcagcaacgg ttgttgttgc ataagaaata      60
aaagaaaatg ccaataggat atcggcattt tcttttgcgt tttt                      104
```

```
<210> SEQ ID NO 3
<211> LENGTH: 70
<212> TYPE: DNA
<213> ORGANISM: Artificial Sequence
<220> FEATURE:
<223> OTHER INFORMATION: Synthetic PCR Primer SD133

<400> SEQUENCE: 3
ttgatttcct gaccctgcca ggctaccgcc tgttagcgta aaccaccaca taactgcaac    60
aacaaccgtt                                                          70

<210> SEQ ID NO 4
<211> LENGTH: 70
<212> TYPE: DNA
<213> ORGANISM: Artificial Sequence
<220> FEATURE:
<223> OTHER INFORMATION: Synthetic PCR Primer SD134

<400> SEQUENCE: 4
ccggatgcgg cgtgaacgcc ttatccggcc tacagtcagc aacggttgtt gttgcagtta    60
tgtggtggtt                                                          70

<210> SEQ ID NO 5
<211> LENGTH: 20
<212> TYPE: DNA
<213> ORGANISM: Artificial Sequence
<220> FEATURE:
<223> OTHER INFORMATION: Synthetic PCR Primer SD58

<400> SEQUENCE: 5
gccgatatcc tattggcatt                                               20

<210> SEQ ID NO 6
<211> LENGTH: 22
<212> TYPE: DNA
<213> ORGANISM: Artificial Sequence
<220> FEATURE:
<223> OTHER INFORMATION: Synthetic PCR Primer SD135

<400> SEQUENCE: 6
accacttccg atgagttaat tg                                            22

<210> SEQ ID NO 7
<211> LENGTH: 22
<212> TYPE: DNA
<213> ORGANISM: Artificial Sequence
<220> FEATURE:
<223> OTHER INFORMATION: Synthetic PCR Primer SD136

<400> SEQUENCE: 7
ctcatcagga gcagagaatt gc                                            22

<210> SEQ ID NO 8
<211> LENGTH: 20
<212> TYPE: DNA
<213> ORGANISM: Artificial Sequence
<220> FEATURE:
<223> OTHER INFORMATION: Synthetic PCR Primer SD137

<400> SEQUENCE: 8
gtttctccca ggggcgtttt                                               20

<210> SEQ ID NO 9
```

<211> LENGTH: 7929
<212> TYPE: DNA
<213> ORGANISM: Escherichia coli
<220> FEATURE:
<221> NAME/KEY: misc_feature
<222> LOCATION: (1545)..(1545)
<223> OTHER INFORMATION: n is a, c, g, or t; Plasmid pLO14151 used as a template in PCR for Cat - SacB cassette.
<220> FEATURE:
<221> NAME/KEY: misc_feature
<222> LOCATION: (3474)..(3475)
<223> OTHER INFORMATION: n is a, c, g, or t; Plasmid pLO14151 used as a template in PCR for Cat - SacB cassette.

<400> SEQUENCE: 9

```
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgccaa gcttgcatgc ctgcaggtcg    420
actctagagg atccccgggt accgagctcg aattcccgcg cccgatgaat tgatccgaag    480
ttcctattct ctagaaagta taggaacttc gaattgtcga caagctagca gtgacggaa    540
gatcacttcg cagaataaat aaatcctggt gtccctgttg ataccgggaa gccctgggcc    600
aactttggc gaaaatgaga cgttgatcgg cacgtaagag gttccaactt tcaccataat    660
gaaataagat cactaccggg cgtatttttt gagttatcga gattttcagg agctaaggaa    720
gctaaaatgg agaaaaaaat cactggatat accaccgttg atatatccca atggcatcgt    780
aaagaacatt ttgaggcatt tcagtcagtt gctcaatgta cctataacca gaccgttcag    840
ctggatatta cggccttttt aaagaccgta agaaaaata gcacaagtt ttatccggcc    900
tttattcaca ttcttgcccg cctgatgaat gctcatccgg aattccgtat ggcaatgaaa    960
gacggtgagc tggtgatatg ggatagtgtt caccccttgtt acaccgtttt ccatgagcaa   1020
actgaaacgt tttcatcgct ctggagtgaa taccacgacg atttccggca gtttctacac   1080
atatattcgc aagatgtggc gtgttacggt gaaaacctgg cctatttccc taaagggttt   1140
attgagaata tgttttttcgt ctcagccaat ccctgggtga gtttcaccag ttttgattta   1200
aacgtggcca atatggacaa cttcttcgcc cccgttttca ccatgggcaa atattatacg   1260
caaggcgaca aggtgctgat gccgctggcg attcaggttc atcatgccgt tgtgatggc    1320
ttccatgtcg gcagaatgct taatgaatta acagtact gcgatgagtg gcagggcggg    1380
gcgtaattt tttaaggcag ttattggtgc ccttaaacgc ctggtgctac gcctgaataa    1440
gtgataataa gcggatgaat ggcagaaatt cgaaagcaaa ttcgacccgg tcgtcggttc    1500
agggcagggt cgttaaatag ccgcttatgt ctattgctgg tttantcggt acccggggat    1560
cgcggccgcg gaccggatcc catcacatat acctgccgtt cactattatt tagtgaaatg    1620
agatattatg atattttctg aattgtgatt aaaaaggcaa ctttatgccc atgcaacaga    1680
aactataaaa aatacagaga atgaaaagaa acagatagat ttttttagttc tttaggcccg    1740
tagtctgcaa atcctttat gattttctat caaacaaag aggaaaatag accagttgca     1800
atccaaacga gagtctaata gaatgaggtc gaaaagtaaa tcgcgcgggt ttgttactga    1860
taaagcaggc aagacctaaa atgtgtaaag ggcaaagtgt atactttggc gtcaccccctt   1920
```

```
acatatttta ggtcttttt  tattgtgcgt aactaacttg ccatcttcaa acaggagggc   1980
tggaagaagc agaccgctaa cacagtacat aaaaaaggag acatgaacga tgaacatcaa   2040
aaagtttgca aaacaagcaa cagtattaac ctttactacc gcactgctgg caggaggcgc   2100
aactcaagcg tttgcgaaag aaacgaacca aaagccatat aaggaaacat acggcatttc   2160
ccatattaca cgccatgata tgctgcaaat ccctgaacag caaaaaaatg aaaaatatca   2220
agttcctgaa ttcgattcgt ccacaattaa aaatatctct tctgcaaaag gcctggacgt   2280
ttgggacagc tggccattac aaaacgctga cggcactgtc gcaaactatc acggctacca   2340
catcgtcttt gcattagccg gagatcctaa aaatgcggat gacacatcga tttacatgtt   2400
ctatcaaaaa gtcggcgaaa cttctattga cagctggaaa aacgctggcc gcgtctttaa   2460
agacagcgac aaattcgatg caaatgattc tatcctaaaa gaccaaacac aagaatggtc   2520
aggttcagcc acatttacat ctgacggaaa aatccgttta ttctacactg atttctccgg   2580
taaacattac ggcaaacaaa cactgacaac tgcacaagtt aacgtatcag catcagacag   2640
ctctttgaac atcaacggtg tagaggatta taaatcaatc tttgacggtg acggaaaaac   2700
gtatcaaaat gtacagcagt tcatcgatga aggcaactac agctcaggcg acaaccatac   2760
gctgagagat cctcactacg tagaagataa aggccacaaa tacttagtat ttgaagcaaa   2820
cactggaact gaagatggct accaaggcga agaatcttta tttaacaaag catactatgg   2880
caaaagcaca tcattcttcc gtcaagaaag tcaaaaactt ctgcaaagcg ataaaaaacg   2940
cacggctgag ttagcaaacg gcgctctcgg tatgattgag ctaaacgatg attacacact   3000
gaaaaaagtg atgaaaccgc tgattgcatc taacacagta acagatgaaa ttgaacgcgc   3060
gaacgtcttt aaaatgaacg gcaaatggta cctgttcact gactcccgcg atcaaaaat   3120
gacgattgac ggcattacgt ctaacgatat ttacatgctt ggttatgttt ctaattcttt   3180
aactggccca tacaagccgc tgaacaaaac tggccttgtg ttaaaaatgg atcttgatcc   3240
taacgatgta acctttactt actcacactt cgctgtacct caagcgaaag gaaacaatgt   3300
cgtgattaca agctatatga caaacagagg attctacgca gacaaacaat caacgtttgc   3360
gccaagcttc ctgctgaaca tcaaaggcaa gaaaacatct gttgtcaaag acagcatcct   3420
tgaacaagga caattaacag ttaacaaata aaaacgcaaa agaaaatgcc gatnnccggt   3480
ttattgacta ccggaagcag tgtgaccgtg tgcttctcaa atgcctcagg ctgtctatgt   3540
gtgactgttg agctgtaaca agttgtctca ggtgttcaat ttcatgttct agttgctttg   3600
ttttactggt ttcacctgtt ctattaggtg ttacatgctg ttcatctgtt acattgtcga   3660
tctgttcatg gtgaacagct ttaaatgcac caaaactcg taaaagctct gatgtatcta   3720
tctttttac accgttttca tctgtgcata tggacagttt tccctttgat gctagcttgc   3780
atgcctgcag gtcgactcta gaggatcccc gtactatcaa caggttgaac tgcggatctt   3840
gcggccagct ttatgcttgt aaaccgtttt gtgaaaaat ttttaaaata aaaaagggga   3900
cctctagggt ccccaattaa ttagtaatat aatctattaa aggtcattca aaaggtcatc   3960
caccggatca attcccctgc tcgcgcaggc tgggtgccaa gctctcgggt aacatcaagg   4020
cccgatcctt ggagcccttg ccctcccgca cgatgatcgt gccgtgatcg aaatccagat   4080
ccttgacccg cagttgcaaa ccctcactga tccggctcac ggtaactgat gccgtatttg   4140
cagtaccagc gtacggccca cagaatgatg tcacgctgaa aatgccggcc tttgaatggg   4200
ttcatgtgca gctccatcag caaaagggga tgataagttt atcaccaccg actatttgca   4260
```

-continued

```
acagtgccgt tgatcgtgct atgatcgact gatgtcatca gcggtggagt gcaatgtcgt    4320
gcaatacgaa tggcgaaaag ccgagctcat cggtcagctt ctcaaccttg gggttacccc    4380
cggcggtgtg ctgctggtcc acagctcctt ccgtagcgtc cggcccctcg aagatgggcc    4440
acttggactg atcgaggccc tgcgtgctgc gctgggtccg ggagggacgc tcgtcatgcc    4500
ctcgtggtca ggtctggacg acgagccgtt cgatcctgcc acgtcgcccg ttacaccgga    4560
ccttggagtt gtctctgaca cattctggcg cctgccaaat gtaaagcgca gcgcccatcc    4620
atttgccttt gcggcagcgg ggccacaggc agagcagatc atctctgatc cattgcccct    4680
gccacctcac tcgcctgcaa gcccggtcgc ccgtgtccat gaactcgatg ggcaggtact    4740
tctcctcggc gtgggacacg atgccaacac gacgctgcat cttgccgagt tgatggcaaa    4800
ggttccctat ggggtgccga gacactgcac cattcttcag gatggcaagt tggtacgcgt    4860
cgattatctc gagaatgacc actgctgtga gcgctttgcc ttggcggaca ggtggctcaa    4920
ggagaagagc cttcagaagg aaggtccagt cggtcatgcc tttgctcggt tgatccgctc    4980
ccgcgacatt gtgcgacag ccctgggtca actgggccga gatccgttga tcttcctgca    5040
tccgccagag ggcgggatgc gaagaatgcg atgccgctcg ccagtcgatt ggctgagctc    5100
atgagcggag aacgagatga cgttggaggg gcaaggtcgc gctgattgct ggggcaacac    5160
gtgaaaggcg agatcaccaa ggtagtcggc aaataatgtc taacaattcg ttcaagccga    5220
cgccgcttcg cggcgcggct taactcaagc gttagatgca ctaagcacat aattgctcac    5280
agccaaacta tcaggtcaag tctgctttta ttatttttaa gcgtgcataa taagccctac    5340
acaaattggg agatatatca tgaaaggctg gcttttttctt gttatcgcaa tagttggcga    5400
agtaatcgca acatccgcat taaaatctag cgagggcttt actaagctga tccggtggat    5460
gacctttga atgacctta atagattata ttactaatta attggggacc ctagaggtcc    5520
ccttttttat tttaaaaatt ttttcacaaa acggtttaca agcataaagc tcgatgaatt    5580
gatccgaagt tcctattctc tagaaagtat aggaacttcg aattgtcgac aagctccccg    5640
gggagcttga tctggcttat cgaaattaat acgactcact atagggagac cggaattcgt    5700
aatcatggtc atagctgttt cctgtgtgaa attgttatcc gctcacaatt ccacacaaca    5760
tacgagccgg aagcataaag tgtaaagcct ggggtgccta atgagtgagc taactcacat    5820
taattgcgtt gcgctcactg cccgctttcc agtcgggaaa cctgtcgtgc cagctgcatt    5880
aatgaatcgg ccaacgcgcg gggagaggcg gtttgcgtat tgggcgctct ccgcttcct    5940
cgctcactga ctcgctgcgc tcggtcgttc ggctgcggcg agcggtatca gctcactcaa    6000
aggcggtaat acggttatcc acagaatcag gggataacgc aggaaagaac atgtgagcaa    6060
aaggccagca aaaggccagg aaccgtaaaa aggccgcgtt gctggcgttt ttccataggc    6120
tccgcccccc tgacgagcat cacaaaaatc gacgctcaag tcagaggtgg cgaaacccga    6180
caggactata aagataccag gcgtttcccc ctggaagctc cctcgtgcgc tctcctgttc    6240
cgaccctgcc gcttaccgga tacctgtccg cctttctccc ttcgggaagc gtggcgcttt    6300
ctcaaagctc acgctgtagg tatctcagtt cggtgtaggt cgttcgctcc aagctgggct    6360
gtgtgcacga accccccgtt cagcccgacc gctgcgcctt atccggtaac tatcgtcttg    6420
agtccaaccc ggtaagacac gacttatcgc cactggcagc agccactggt aacaggatta    6480
gcagagcgag gtatgtaggc ggtgctacag agttcttgaa gtggtggcct aactacggct    6540
acactagaag aacagtattt ggtatctgcg ctctgctgaa gccagttacc ttcggaaaaa    6600
gagttggtag ctcttgatcc ggcaaacaaa ccaccgctgg tagcggtggt ttttttgttt    6660
```

```
gcaagcagca gattacgcgc agaaaaaaag gatctcaaga agatcctttg atcttttcta      6720
cggggtctga cgctcagtgg aacgaaaact cacgttaagg gattttggtc atgagattat      6780
caaaaaggat cttcacctag atccttttaa attaaaaatg aagttttaaa tcaatctaaa      6840
gtatatatga gtaaacttgg tctgacagtt accaatgctt aatcagtgag gcacctatct      6900
cagcgatctg tctatttcgt tcatccatag ttgcctgact ccccgtcgtg tagataacta      6960
cgatacggga gggcttacca tctggcccca gtgctgcaat gataccgcga gacccacgct      7020
caccggctcc agatttatca gcaataaacc agccagccgg aagggccgag cgcagaagtg      7080
gtcctgcaac tttatccgcc tccatccagt ctattaattg ttgccgggaa gctagagtaa      7140
gtagttcgcc agttaatagt ttgcgcaacg ttgttgccat tgctacaggc atcgtggtgt      7200
cacgctcgtc gtttggtatg gcttcattca gctccggttc ccaacgatca aggcgagtta      7260
catgatcccc catgttgtgc aaaaaagcgg ttagctcctt cggtcctccg atcgttgtca      7320
gaagtaagtt ggccgcagtg ttatcactca tggttatggc agcactgcat aattctctta      7380
ctgtcatgcc atccgtaaga tgcttttctg tgactggtga gtactcaacc aagtcattct      7440
gagaatagtg tatgcggcga ccgagttgct cttgccggc gtcaatacgg gataataccg       7500
cgccacatag cagaacttta aaagtgctca tcattggaaa acgttcttcg gggcgaaaac      7560
tctcaaggat cttaccgctg ttgagatcca gttcgatgta acccactcgt gcacccaact      7620
gatcttcagc atcttttact ttcaccagcg tttctgggtg agcaaaaaca ggaaggcaaa      7680
atgccgcaaa aaagggaata agggcgacac ggaaatgttg aatactcata ctcttcctt       7740 ttcaatatta ttgaagcatt tatcagggtt attgtctcat gagcggatac atatttgaat      7800
gtatttagaa aaataaacaa ataggggttc cgcgcacatt tccccgaaaa gtgccacctg      7860
acgtctaaga aaccattatt atgatgacat taacctataa aaataggcgt atcacgaggc      7920
cctttcgtc                                                             7929
```

ORGANIC ACID PRODUCTION IN MICROORGANISMS BY COMBINED REDUCTIVE AND OXIDATIVE TRICABOXYLIC ACID CYLCE PATHWAYS

CROSS-REFERENCE TO RELATED APPLICATIONS

The application is the U.S. national stage application of International Patent Application No. PCT/US2010/057291, which claims the priority of the U.S. Provisional Application Ser. No. 61/281,486, filed on Nov. 18, 2009.

The Sequence Listing for this application is labeled "SeqList.txt" which was created on Nov. 17, 2010 and is 240 KB. The entire content of the sequence listing is incorporated herein by reference in its entirety.

BACKGROUND OF THE INVENTION

Succinic acid is an intermediate in the tricarboxylic acid (TCA) cycle. Many bacteria are known to have natural ability to produce succinate as a fermentation product. The commercial demand for succinic acid is expanding. Succinic acid is used as a starting material in the manufacture of number of specialty chemicals such as 1,4-butanediol, tetrahydrofuran, γ-butryolactone and N-methylpyrrolidone.

A 2004 U.S. Department of Energy report entitled "Top value added chemicals from biomass" has identified succinic acid as one of the twelve building block chemicals that can be produced from renewable feedstock.

Currently, succinic acid is produced chemically from butane through maleic anhydride. The fermentative production of succinic acid from renewable feedstock is expected to become increasingly competitive with the rising oil price. Microbiological production of succinic acid has been reported with the rumen bacteria such as *Actinobacillus succinogens*, *Anaerobiosprillum succiniproducens*, *Mannheimia succiniproducens*, and *Basfia succiniproducens* (Scholten et al. (2009). Succinic acid production by these naturally occurring rumen bacteria depends on complex growth medium with expensive ingredients, which increases cost associated with the commercial production of succinic acid. In order to overcome these economic limitations associated with rumen bacteria, efforts have been made to engineer strains of *Escherichia coli* for commercial succinic acid production. For example, the *E. coli* strain K J122 for the production of succinic acid, described in by Jantama et at (2008a; 2008b) and in the International Patent Applications published under the Patent Cooperation Treaty Nos. WO 2008/115958 and WO 2010/115067, can grow on a minimal medium using glucose as the source of carbon.

Efforts have also been made to use eukaryotic microorganisms in the commercial fermentative production of succinic acid. International Patent Application Publication published on May 28, 2009 under Patent Cooperation Treaty with No. WO 2009/065777 describes a filamentous fungus genetically modified to produce a dicarboxylic acid. International Patent Application Publication published on May 28, 2009 under Patent Cooperation Treaty with No. WO 2009/065718 provides yeast strain with the genetic modification useful in the production of succinic acid.

In wild type *E. coli* grown under aerobic conditions, the carbon substrates such as glucose are fully oxidized. Further, the reduced cofactor pool (NADH) resulting from the complete oxidation of the substrate is oxidized through oxidative phosphorylation. On the other hand, under anaerobic condition the carbon substrates are only partially oxidized and fermentation products such as ethanol, lactate, acetate, formate, and succinate accumulate in the bacterial cells and fermentation broth. The efficiency of a genetically modified *E. coli* strain to produce succinic acid depends on carbon partition between various end products. Thus the efficiency of succinic acid production can be enhanced by blocking carbon entry into the other end products of fermentation. In addition to channeling the carbon flow into succinic acid, it is necessary to maintain the redox balance of the cell so that carbon flow from sugars to succinic acid occurs at high efficiency. During an anaerobic or microaerobic fermentation where the carbon source is one or more sugars, and where oxidative phosphorylation is absent or at a low level, cells need a biochemical mechanism for re-oxidizing the reduced compound NADH (and other similar reduced compounds such as FADH and NADPH) that is generated by the glycolytic pathway from sugar to pyruvate, For a cell to grow or live during an anaerobic or microaerobic fermentation, the net rates of oxidation of NADH to NAD and chemical reduction of NAD to NADH must be equal. Otherwise, the intracellular pool of either NADH or NAD will become depleted, and growth and metabolism will cease. A cell in which the net rates of oxidation of NADH to NAD and chemical reduction of NAD to NADH are equal is said to be "redox balanced". Redox balance is more important to maintain under anaerobic or microaerobic conditions than under aerobic conditions, since when oxygen is present, any excess NADH can be oxidized by oxidative phosphorylation, and any deficit can be filled by running the oxidative TCA cycle.

In order to obtain commercially attractive yields of succinate, *E. coli* is grown anaerobically or microaerobically. Under microaerobic conditions, the fermentor can be exposed to the outside air through vents in the fermentor used for reagent exchange. In recent years, a method for producing succinate under aerobic condition has been described. U.S. Pat. No. 7,244,610 describes the aerobic succinate production using *E. coli* bacteria. When the bacteria are grown aerobically, the succinic acid production is achieved by means of blocking the normal operation of the oxidative tricarboxylic acid cycle through genetic manipulations. Thus under aerobic conditions, the deletion of the sdhA gene decreases oxidation of succinic acid into fumaric acid leading to the accumulation of succinic acid.

Two stage fermentations for producing succinate is also well known in the art. In the two stage fermentations, the bacterium is grown aerobically to achieve a certain cell mass followed by transfer to an anaerobic condition to start the succinic acid production. During the anaerobic production stage, the headspace of the fermentor is filled with carbon dioxide, hydrogen or a mixture of both gases. Thus in two stage fermentation, the bacterial growth phase is uncoupled from the succinate production phase.

Irrespective of the conditions used for the growth and succinic acid production, the succinic acid production in *E. coli* occurs through one of the three pathways illustrated in FIG. 1. As shown in FIG. 1, the central metabolic pathway starts with the glucose uptake. The wild type *E. coli* cells use an enzyme complex known as a phosphotransferase system (PTS) to transport the glucose from the medium into the cell. The PTS for glucose transport, for example, is a multi protein complex consisting of the PtsG, PtsI, PtsH and Crr proteins. The PTS system requires a molecule of phosphoenol pyruvate (PEP) for every molecule of glucose transported into the cell and yields a molecule of pyruvate for every molecule of PEP consumed. The glucose molecule transported into the cell is phosphorylated and ultimately two molecules of PEP are derived from each of the glucose molecule transported into the cell. Thus, of the two molecules of PEP that could be derived from a single glucose molecule, one molecule of PEP is consumed when the glucose uptake occurs through PTS and only one molecule of PEP is available for the central metabolic pathway to produce succinic acid. Thus the glucose uptake through PTS is an energy-intensive process that utilizes PEP substrate needed for succinic acid production and could reduce the efficiency of succinic acid production when using *E. coli* as a biocatalyst. This decrease in the efficiency of succinic acid production due to the PEP requirement at the level of glucose uptake is overcome by decreasing the activity of one or more of the genes such as ptsG, ptsI, ptsH and crr, which code for the polypeptides of the glucose PTS.

In the absence of a PTS, glucose and other sugars can be imported by an alternative sugar transporter located in the cytoplasmic membrane. One class of non-PTS transporters are the family of ATP binding cassette (ABC) transporters, which use ATP for energy. Another class of non-PTS transporters is the family of symporters that use an ion gradient (for example a proton gradient) for energy. A third class of non-PTS transporters is the family of facilitated diffusers, which requires no energy, but instead relies on a simple concentration gradient. For the non-PTS transporters, the imported sugar needs to be phosphorylated by a sugar kinase such as glucokinase, encoded by the glk gene. When the PTS is mutated, more of the PEP derived from glucose becomes available for biosynthesis, which in turn can increase the efficiency of production of certain chemicals such as succinate.

PEP can enter into the tricarboxylic acid cycle leading to the production of succinic acid by three different routes. In first pathway to succinate production, referred as the "reductive TCA" pathway for succinic acid production, PEP is carboxylated to oxaloacetic acid (OAA) by PEP carboxykinase or PEP carboxylase. The oxalaoacetic acid is reduced to malate which in turn is converted into fumarate. Fumarate is subsequently reduced to succinic acid. Thus through the reductive TCA pathway using PEP carboxykinase, succinic acid production is coupled with the oxidation of two molecules of NADH. This reductive pathway using PEP carboxykinase for succinate production is also reported to be present in the rumen bacteria Mannhaemia succiniproducens (Lee et al., 2005).

In the second pathway for succinic acid production, a molecule of PEP derived from glucose can be converted into pyruvate which in turn produces a molecule of acetyl-CoA. The acetyl-CoA thus produced can combine with the molecule of OAA to produce citrate which is isomerized to isocitrate. The isocitrate is decarboxylated to produce 2-ketoglutaric acid which is subjected to another decarboxylation reaction to yield succinyl-CoA, which is then converted to succinic acid. This second pathway for succinic acid production is referred as the "oxidative TCA" pathway for succinic acid production.

The third pathway for succinic acid production present in *E. coli* is known as the "glyoxylate shunt", also known in some literature as the glyoxylate bypass. The glyoxylate shunt starts with isocitrate formed in the oxidative part of tricarboxylic acid cycle. The enzyme isocitrate lyase (encoded by aceA) cleaves isocitrate into succinate and glyoxylate. The glyoxylate combines with a molecule of acetyl-CoA, catalyzed by malate synthase (encoded by aceB), which results in the formation of a molecule of malate. Depending on the circumstances, the malate thus formed can be converted into fumarate, which in turn is reduced to succinate as in the reductive pathway for succinic acid production, or the malate thus formed can be oxidized to oxaloacetate, which can then combine with a second molecule of acetyl-CoA to enter the oxidative TCA pathway. This pathway, which has the net effect of converting two acetyl-CoA's and one NAD into one succinate and one NADH, is referred to as the "glyoxylate shunt". The acetyl-CoA that feeds in to the glyoxylate shunt can come from pyruvate via pyruvate dehydrogenase, which also produces an NADH. Thus, when carbon flows from a sugar to succinate through the glyoxylate shunt, there is net production of NADH from NAD.

The maximum theoretical succinate yield in a redox balanced cell is 1.714 mol of succinate from 1 mol of glucose, which is equivalent to a mass yield of 1.12 grams of succinate for one gram of glucose consumed. This theoretical succinate yield is possible when the carbon flow through the central metabolic pathway is accompanied by appropriate redox balance. It has been reported that the maximum succinate production requires 71.4% of the carbon flow to OAA and 28.6% of the carbon flow to acetyl-CoA. (Vemuri et al., 2002a). Because the reductive TCA pathway to succinate requires a net input of two moles of NADH per mole glucose metabolized into succinate, and the glyoxylate shunt produces a net output of 5 moles of NADH per mole of glucose metabolized into succinate, it has been dogma in the prior art that redox balance for anaerobic or microaerobic succinate production from sugars in both bacteria and yeast is achieved by running a combination of the reductive TCA pathway and the glyoxylate shunt (Vemuri et al., 2002a; Sanchez et al., 2005; Wang et al., 2006; Martinez et al., 2010; Jansen et al., 2010). In fact, the flux models in these prior art disclosures do not even include the oxidative TCA pathway. This dogma was derived from earlier dogma that stated that a key enzyme in the oxidative TCA pathway, 2-ketoglutarate dehydrogenase "is virtually absent during anaerobic growth" (Cronan and Laporte, 1996).

In the prior art references cited above, succinate titers did not exceed 20 g/l, and the fermentation conditions required a rich medium. These titers are not high enough to be commercially attractive. Thus there has been a need for strains that produce succinate with increased efficiency. The strains of the present invention produce more than 20 g/l succinate in a minimal glucose medium.

Efforts have been made to enhance the carbon flow through the glyoxylate shunt for the purpose of improving the production of amino acids and chemicals. Two different approaches have been reported to be useful in enhancing the carbon flow through the glyoxylate shunt. In one approach, the enzymes involved in the operation of glyoxylate shunt are over expressed by means of replacing the native promoters with promoters constitutively active in *E. coli*. The two enzymes aceA (isocitrate lyase) and aceB (malate synthase) involved in the operation of glyoxylate shunt are in the aceBAK operon. U.S. Patent Application Publication No. US 2007/0015261 describes an *E. coli* strain expressing aceBAK operon under a constitutive promoter. In the second approach the glyoxylate shunt is activated by inactivating the iclR gene coding for a repressor of aceBAK operon. The inactivation of the iclR gene has been described in the U.S. Pat. Nos. 7,244, 610 and 7,262,046.

In the present invention, the inventors have discovered that inactivation of the glyoxylate shunt had no negative effect, and inactivation of the glyoxylate shunt repressor (encoded by the iclR gene) had no positive effect on succinate production in the engineered *E. coli* succinate production strain KJ122. Deletion of the aceA gene coding for isocitrate lyase, the first enzyme in the glyoxylate shunt had no measurable effect on growth or succinic acid production in fermentors. Deletion of iclR also had no effect on growth or succinate production. Moreover, all attempts to delete any one of several genes encoding an enzyme of the oxidative TCA cycle, using well established methods, failed. Genes that could not be deleted in KJ122, include icd, encoding isocitrate dehydrogenase; gltA, encoding citrate synthase; sucD, encoding succinyl-CoA synthetase, and sdhD, encoding a subunit of succinate dehydrogenase. These results caused the present inventors to conclude that 1) the glyoxylate shunt is irrelevant and dispensable in KJ122, and 2) the oxidative TCA pathway is essential for growth and succinate production in KJ122.

Since the glyoxylate shunt springs from the oxidative part of the tricarboxylic acid cycle, these observations are useful in designing further genetic manipulations both on the oxidative and reductive parts of tricarboxylic acid cycle for the purpose of enhancing the production of succinic acid.

BRIEF SUMMARY OF THE INVENTION

An embodiment of the invention is directed to a method of producing succinic acid in microaerobic and anaerobic conditions by supplying a mutant strain of $E.\ coli$ bacterium that produces at least 1 mole of succinic acid for every mole of glucose consumed. The $E.\ coli$ bacterial strain described in this invention does not have a functional glyoxylate shunt that produces 2 molecules of succinic acid using a molecule of oxaloacetic acid and two molecules of acetyl-CoA.

In a preferred embodiment of the invention, the inhibition of carbon flow through glyoxylate shunt is achieved by deleting the aceA gene coding for isocitrate lyase, the first enzyme in the glyoxylate shunt. In a more preferred embodiment of the present invention, the carbon flow through glyoxylate shunt is inhibited by the deletion or inactivation of either the aceA or aceB gene sequences. In yet another preferred embodiment of the present invention, both aceA and aceB gene sequences are deleted.

In another embodiment of the present invention, the aceK gene coding for a kinase responsible for the phosphorylation of isocitrate dehydrogenase is deleted along with the deletion of aceA and aceB genes.

In yet another embodiment of the present invention, the strain lacking the carbon flow through glyoxylate shunt further comprises mutations in the mgsA and ldhA genes to inhibit the flow of carbon to lactate.

In yet another embodiment of the present invention, besides blocking the carbon flow through the glyoxylate shunt, the carbon flow to acetate is prevented by means of deleting the genes pflB, pta, ack, and poxB.

In yet another embodiment of the present invention, besides blocking the carbon flow through glyoxylate shunt, the carbon flow to ethanol is prevented by deleting the adhE gene.

In a preferred embodiment of the present invention, besides blocking the carbon flow through the glyoxylate shunt, the carbon flow to acetate, ethanol, formate, and lactate are blocked by means of deleting mgsA, ldhA, pflB, poxB, pta, ack, and adhE genes.

In yet another embodiment of the present invention, besides blocking the carbon flow through glyoxylate shunt, the sugar uptake through PTS is decreased by mutating one or more genes coding for the component proteins of PTS for the purpose of conserving PEP for succinic acid production. In a preferred embodiment of the present invention, the sugar uptake through PTS is decreased by mutating one or more genes selected from the group consisting of ptsG, ptsH, ptsI and crr.

A further embodiment of the invention is directed to a method of producing succinic acid using a mutant with deletions in multiple genes including the genes coding for the proteins involved in glyoxylate shunt, lactate production, acetate production, and ethanol production.

In yet another embodiment of the present invention, succinic acid production is enhanced by means of improving the carbon flow from pyruvate to oxaloacetate by means of transforming the bacterial cell selected for succinic acid production with a polynucleotide sequence encoding a pyruvate carboxylase operatively linked to a promoter, wherein said polynucleotide sequence is expressed and produces an enzymatically active pyruvate carboxyalse.

In another embodiment of the present invention, the bacterial strain lacking the carbon flow through the glyoxylate shunt further comprises a deregulated production of PEP carboxykinase enhancing the flow of the carbon from PEP to oxaloacetate.

In yet another embodiment of the present invention, a bacterial strain with an enlarged flux to oxaloacetate further comprises enzymes that would facilitate the conversion of oxaloacetate to succinic acid through malate and fumarate in the reductive arm of the tricarboxylic acid. In a preferred embodiment of the invention, the $E.\ coli$ strain producing at least 1 mol of succinic acid per mol of glucose lacking a carbon flow through glyoxylate shunt further comprises malate dehydrogenase, fumarase and fumarate reductase enzymes with an enhanced activity for the efficient conversion of oxaloacetate to succinate.

BRIEF DESCRIPTION OF THE DRAWINGS

FIG. 4. The oxidative TCA pathway is more efficient than the glyoxylate shunt for succinate synthesis. Stoichiometries of three different pathways from glucose to succinate are given. Two combinations that lead to redox balance are also given.

DETAILED DESCRIPTION OF PREFERRED EMBODIMENTS

Figure 1:
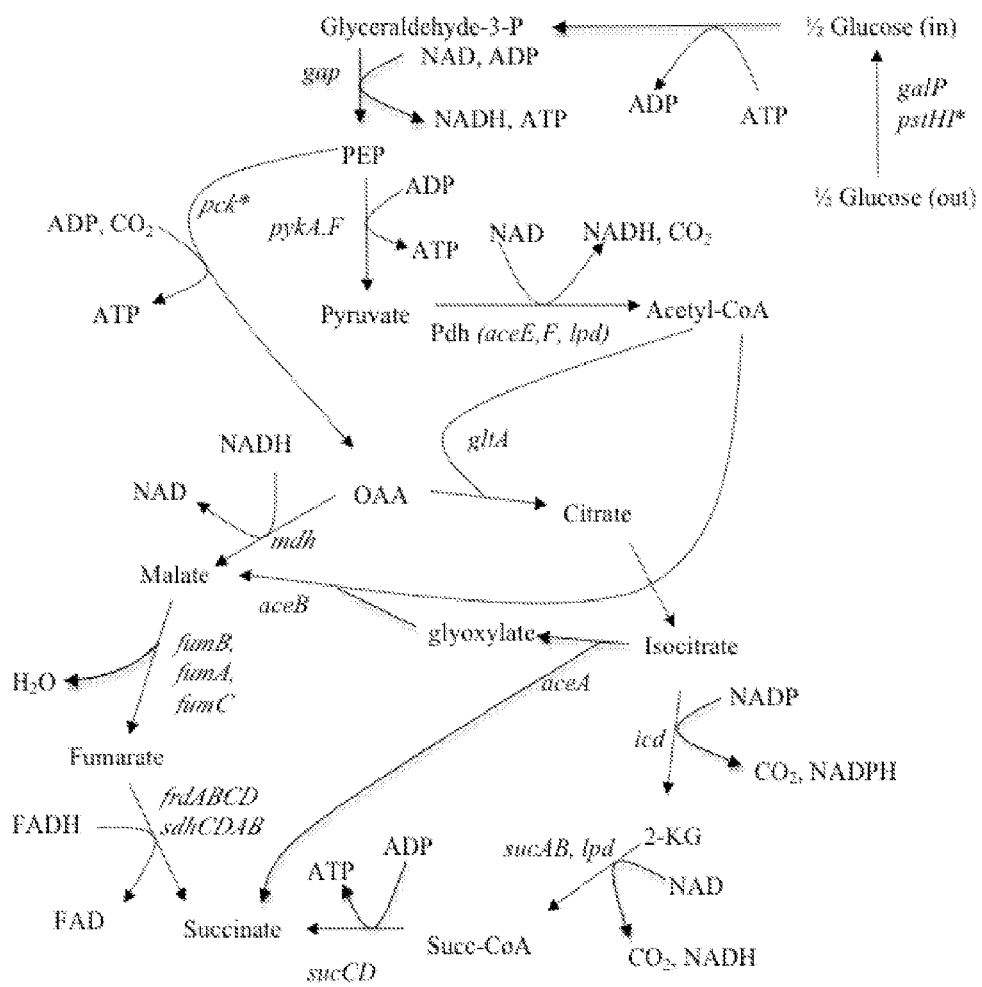
FIG. 1. Carbon flow from glucose to succinate in microorganisms. Flow from other carbon sources, such as glycerol and other sugars is similar for the lower parts of the pathway involving the TCA cycle and glyoxylate shunt, which are relevant for the present invention. Shown in this figure are the genes encoding relevant enzymes in $E.\ coli$, but the pathway is the same for most microorganisms. The carbon enters the tricarboxylic acid as oxaloacetic acid or as acetyl-CoA. Succinate is derived from oxaloacetic acid or acetyl-CoA through three different pathways. The oxidative TCA pathway for succinate production is shown on the right side of the tricarboxylic acid cycle and involves the intermediates citrate, isocitrate, 2-ketoglutaric acid, succinyl-CoA. The reductive TCA pathway for succinate production is shown on the left side of the tricarboxylic acid cycle and involves the intermediates malate and fumarate. The glyoxylate shunt for the production of succinate involves the isocitrate lyase enzyme (encoded by aceA, malate synthase enzyme (encoded by aceB) and acetyl-CoA.

A number of industrially useful chemicals can be manufactured using the present invention. Examples of such chemicals include, but are not limited to, ethanol, butanols, lactate, succinate, fumarate, malate, threonine, methionine and lysine. Since organic acids can exist both as free acids and as salts (for example, but not limited to, salts of sodium, potassium, magnesium, calcium, ammonium, chloride, sulfate, carbonate, bicarbonate, etc), chemical names such as succinic acid, fumaric acid, malic acid, aspartic acid, threonine, methionine, and lysine shall be meant to include both the free acid and any salt thereof. Likewise, any salt, such as succinate, fumarate, malate, aspartate, etc., shall be meant to include the free acid as well.

One of the objectives of the present invention is to increase the efficiency of organic acid production by microorganisms. The term "efficiency" is meant to include, without limitation rate, titer, or yield of organic acid production. The term "organic acid" is meant to include, without limitation, succinic acid, malic acid, fumaric acid, lactic acid, aspartic acid, threonine, methionine, lysine, isoleucine, or any derivative of those acids. The term "organic acid" is also meant to include any salt of any organic acid, including, but not limited to, sodium, potassium, calcium, magnesim, ammonium, carbonate, bicarbonate, chloride, phosphate, and sulfate salts.

As used in the present invention, the term "titer" means the molar concentration of a particular compound in the fermentation broth. Thus in the fermentation process for the production of succinic acid according to the present invention, a succinic acid titer of 100 mM would mean that the fermentation broth at the time of measurement contained 100 mMoles of succinic acid per liter of fermentation broth.

As used in the present invention, the term "yield" refers to the moles of a particular compound produced per mole of the feedstock consumed during the fermentation process. Thus in the fermentative process for the production of succinic acid using glucose as the feedstock, the term yield refers to the number of moles of succinic acid produced per mole of glucose consumed.

As used in the present invention, the term "volumetric productivity" refers to the amount of a particular compound in grams produced per unit volume per unit time. Thus a volumetric productivity value of 0.9 g $L^{-1}h^{-1}$ for succinic acid would mean that 0.9 gram succinic acid is accumulated in one liter of fermentation broth during an hour of growth.

The term microorganism (which is equivalent to the term "microbial strain") is meant to include, but not be limited to, any bacterium, archeon, yeast, filamentous fungus, alga, diatom, or dinoflagellate.

The recombinant microorganisms suitable for this present invention are derived from a number of bacterial families, preferably from the Enterobacteriaceae family. The suitable microorganisms are selected form the genera *Escherichia*, *Erwinia*, *Providencia*, and *Serratia*. The genus *Escherichia* is particularly preferred. Within the genus *Escherichia*, the species *Escherichia coli* is particularly preferred. Any one strain of *E. coli* such as *E. coli* B, *E. coli* C, *E. coli* W, or the like is useful for the present invention.

In some other embodiments of the invention, bacteria that can be modified according to the present invention include, but are not limited to, *Achromobacter delmarvae*, *Achromobacter viscosus*, *Achromobacter lacticum*, *Actinomadura madurae*, *Actinomyces violaceochromogenes*, *Aeromonas salmonicida*, *Agrobacterium tumefaciens*, *Agrobacterium radiobacter*, *Alcaligenes faecalis*, *Arthrobacter citreus*, *Arthrobacter tumescens*, *Arthrobacter paraffineus*, *Arthrobacter hydrocarboglutamicus*, *Arthrobacter oxydans*, *Aureobacterium saperdae*, *Azotobacter indicus*, *Bacillus amyloliqyefaciens*, *Bacillus coagulans*, *Bacillus circulans*, *Bacillus licheniformis*, *Bacillus pumilus*, *Bacillus subtilis*, *Bacillus thiaminolyticus*, *Brevibacterium ammoniagenes*, *divaricatum*, *Brevibacterium lactofermentum*, *Brevibacterium flavum*, *Brevibacterium globosum*, *Brevibacterium fuscum*, *Brevibacterium ketoglutamicum*, *Brevibacterium helcolum*, *Brevibacterium pusillum*, *Brevibacterium testaceum*, *Brevibacterium roseum*, *Brevibacterium immariophilium*, *Brevibacterium linens*, *Brevibacterium protopharmiae*, *Citrobactor freundii*, *Corynebacterium acetophilum*, *Corynebacterium glutamicum*, *Corynebacterium callunae*, *Corynebacterium acetoacidophilum*, *Corynebacterium acetoglutamicum*, *Enterobacter aerogenes*, *Erwinia amylovora*, *Erwinia carotovora*, *Erwinia herbicola*, *Erwinia chrysanthemi*, *Escherichia freundii*, *Flavobacterium peregrinum*, *Flavobacterium fucatum*, *Flavobacterium aurantinum*, *Flavobacterium rhenanum*, *Flavobacterium sewanense*, *Flavobacterium breve*, *Flavobacterium meningosepticum*, *Gluconobacter oxydans*, *Gluconobacter asaii*, *Kitasatosporia parulosa*, *Klebsiella oxytoca*, *Klebsiella pneumonieae*, *Microbacterium ammoniaphilum*, *Micrococcus* sp. CCM825, *Morganella morganii*, *Nocardia opaca*, *Nocardia rugosa*, *Planococcus eucinatus*, *Proteus rettgeri*, *Propionibacterium shermanii*, *Pseudomonas synxantha*, *Pseudomonas azotoformans*, *Pseudomonas fluorescens*, *Pseudomonas ovalis*, *Pseudomonas stutzeri*, *Pseudomonas acidovolans*, *Pseudomonas mucidolens*, *Pseudomonas testosteroni*, *Pseudomonas aeruginosa*, *Rhodococcus erythropolis*, *Rhodococcus rhodochrous*, *Rhodococcus* sp. ATCC 15592, *Rhodococcus* sp. ATCC 19070, *Serratia marcescens*, *Sporosarcina ureae*, *Staphylococcus aureus*, *Streptomyces coelicolor*, *Streptomyces flavelus*, *Streptomyces griseolus*, *Streptomyces lividans*, *Streptomyces olivaceus*, *Streptomyces tanashiensis*, *Streptomyces virginiae*, *Streptomyces antibioticus*, *Streptomyces cacaoi*, *Streptomyces lavendulae*, *Streptomyces viridochromogenes*, *Salmonella typhimurium*, *Salmonella schottmulleri*, *Vibrio metschnikovii*, *Vibrio tyrogenes*, *Xanthomonas citri* and so forth.

*E. coli* strains capable of producing organic acids in significant quantities are well known in the art. For example, the U.S. Patent Application Publication No. 2009/0148914 provides strains of *E. coli* as a biocatalyst for the production of chemically pure acetate and/or pyruvate. The U.S. Pat. No. 7,629,162 provide derivatives of *E. coli* K011 strain constructed for the production of lactic acid. International Patent Applications published under the Patent Cooperation Treaty Nos. WO 2008/115958 and WO 2010/115067 provide microorganism engineered to produce succinate and malate in minimal mineral salt medium containing glucose as a source of carbon in pH-controlled batch fermentation.

Biosynthetic production of many chemicals can proceed more efficiently (for example, at higher yield) when the growth of the production organism is carried out under conditions where oxygen or air is absent or limited. Examples of such chemicals include, but are not limited to, ethanol, butanols, lactate, succinate, fumarate, and malate. This is largely because the presence of oxygen generally results in the metabolism of carbon sources into carbon dioxide, a relatively low value byproduct, Fermentation in the absence of a deliberate feeding of oxygen or air is usually called "anaerobic". However, achieving strict anaerobic conditions is costly and sometimes difficult to attain. Moreover, for some fermentations, strict anaerobic conditions are not necessary or sometimes not optimal. For fermentations where oxygen or air is not made strictly absent, or where oxygen or air is deliberately fed at a low, controlled rate, we shall use the term "microaerobic".

The objective of the present invention is to enhance the succinic acid production by fermentation in industrial microbial organisms by means of directing the carbon flow through appropriate sections of the tricarboxylic acid cycle. Although the present invention is described in detail with the examples based on a prokaryotic microorganism, the teachings of the present invention are equally applicable for the industrial production of succinic acid using eukaryotic microorganisms such as filamentous fungi and yeast where the genetic manipulation of central carbon metabolic pathway is practiced in order to achieve the required efficiency for succinic acid production.

The terms "genetically engineered" or "genetically modified" or "genetically manipulated" as used herein refers to the practice of altering the expression of one or more enzymes or proteins in the microorganisms through manipulating the genomic DNA of the microorganisms.

As used in the present invention, the term "gene" includes the open reading frame of the gene as well as the upstream and downstream regulatory sequences. The upstream regulatory region is also referred as the promoter region of the gene. The downstream regulatory region is also referred as the terminator sequence region.

A "Homolog" is a gene related to a second gene by descent from a common ancestral DNA sequence. The term, homolog, may apply to the relationship between genes separated by the event of speciation or to the relationship between genes separated by the event of genetic duplication. "Orthologs" are genes in different species that evolved from a common ancestral gene by speciation. Normally, orthologs retain the same function in the course of evolution. Identification of orthologs is critical for reliable prediction of gene function in newly sequenced genomes. Speciation is the origin of a new species capable of making a living in a new way from the species from which it arose. As part of this process it has also acquired some barrier to genetic exchange with the parent species. "Paralogs" are genes related by duplication within a genome. Orthologs retain the same function in the course of evolution, whereas paralogs evolve new functions, even if these are related to the original one.

A gene or protein with "altered activity" is broadly defined as gene or protein that produces a measurable difference in a measurable property when compared to the relevant wild type gene or protein. The altered activity could manifest itself in a general way by increasing or decreasing the growth rate or efficiency of succinate production of the strain containing the altered gene or protein. Other measurable properties include, but are not limited to enzyme activity, substrate specificity of an enzyme, kinetic parameters of an enzyme such as affinity for a substrate or rate, stability of an enzyme, regulatory properties of an enzyme, gene expression level, regulation of gene expression under various conditions, etc.

As used in the present invention, the term mutation refers to a genetic modification done to any DNA sequence, for example to a gene including the open reading frame, upstream regulatory region and downstream regulatory region. A gene mutation can result either in an up regulation or a down regulation or complete inhibition of the transcription of the open reading frame of the gene. Some kinds of gene mutation can be achieved either by deleting the entire coding region of the gene or a portion of the coding nucleotide sequence or by introducing a frame shift mutation, a missense mutation, or insertion, or by introducing a stop codon or combinations thereof. Mutations may occur in the structural genes coding for the proteins directly involved in the biological functions such as enzyme reactions or transport of the organic molecules across the cell membrane. Alternately, mutations may occur in the regulatory genes coding for the proteins which control the expression of the genes coding for the proteins directly involved in the biological functions. The proteins which control the expression of the other genes are referred to as regulatory proteins and the genes coding for these regulatory proteins are referred to as regulatory genes.

A "null mutation" is a mutation that confers a phenotype that is substantially identical to that of a deletion of an entire open reading frame of the relevant gene, or that removes all measurable activity of the relevant gene.

A "mutant" is a microorganism whose genome contains one or more mutations. A "mutant" is a second microorganism that contains a mutation relative to either 1) a first microorganism which is a wild type microorganism or natural isolate from which the second microorganism was ultimately derived, or 2) a third microorganism that differs from said second microorganism only in that said third microorganism contains a wild type gene at the genetic locus of said mutation. Said second microorganism shall be referred to as a "non-mutant" with reference to said first or said third microorganism. A microorganism can be a mutant with respect to one genetic locus while being a non-mutant with respect to a different genetic locus.

As used in this invention, the term "exogenous" is intended to mean that a DNA sequnces or molecule or an activity derived from outside of a cell is introduced into the host microbial organism. In the case an exogenous nucleic acid molecule introduced into the microbial cell, the introduced nucleic acid may exist as an independent plasmid or may get integrated into the host chromosomal DNA. The exogenous nucleic acid coding for a protein may be introduced into the microbial cell in an expressible form with its own regulatory sequences such as promoter and terminator sequences. Alternatively, the exogenous nucleic acid molecule may get integrated into the host chromosomal DNA and may be under the control of the host regulatory sequences.

The term "endogenous" refers to the molecules and activity that are naturally present within the host cell. When used in reference to a biosynthetic activity, the term "exogenous" refers to an activity that is introduced into the host reference organism. The source can be, for example, a homologous or heterologous encoding nucleic acid that expresses the referenced activity following introduction into the host microbial organism. If the nucleic acid coding for a protein is obtained from the same species of the microbial organism, it is referred as homologous DNA. If the nucleic acid derived from a different microbial species, it is referred as heterologous DNA. Irrespective of the nature of the DNA, whether it is homologous or heterologous, when introduced into a host cell, the DNA as well as the activity derived form that introduced DNA is referred as exogenous. Therefore, exogenous expression of an encoding nucleic acid of the invention can utilize either or both heterologous and homologous encoding nucleic acid.

An embodiment of the invention is directed to a method of producing an organic acid, such as succinic acid, under microaerobic or anaerobic conditions by supplying a mutant strain of E. coli bacterium that produces at least 1 mole of succinic acid for every mole of glucose consumed. A microorganism strain described in this invention has decreased activity of the glyoxylate shunt relative to that of the related wild type strain. In a preferred embodiment of the invention, the decrease of carbon flow through glyoxylate shunt is achieved by decreasing the activity of isocitrate lyase, the first enzyme in the glyoxylate shunt. In *E. coli*, this gene is the aceA gene. The decrease in activity of isocitrate lyase can be accomplished by mutating the gene encoding isocitrate lyase, for example by deleting the gene, but any mutation that decreases the activity of the isocitrate lyase enzyme would be included in the present invention. The foregoing generalizations can also be applied to the other genes and enzymes of the glyoxylate shunt, named below. Thus in another preferred embodiment of the present invention, the carbon flow through glyoxylate shunt is decreased by the decreasing the activity of the malate synthase of the glyoxylate shunt. In *E. coli*, this gene is the aceB gene.

In some organisms, for example *E. coli* and relatives of *E. coli*, flow of carbon from isocitrate into the glyoxylate shunt is positively regulated (increased) by phophorylation of isocitrate dehydrogenase (IDH, encoded by the icd gene), which inhibits IDH, which in turn inhibits carbon from flowing through the oxidative TCA pathway and favors flow of carbon through the glyoxylate shunt. The phosphorylation of IDH is enzymatically catalyzed by IDH kinase, which is encoded by the aceK gene in *E. coli*. Thus, in another embodiment, a decrease in the activity of the glyoxylate shunt, or flow of carbon through the glyoxylate shunt, is accomplished by decreasing the activity of IDH kinase, for example by mutating the gene encoding IDH kinase. In a preferred embodiment of the present invention, all three of the genes coding enzymes of the glyoxylate shunt are deleted, specifically, the genes encoding isocitrate lyase, malate synthase of the glyoxylate shunt, and IDH kinase. In another preferred embodiment, the flow of carbon through the glyoxylate shunt is completely eliminated.

Decreasing the flow of carbon through the glyoxylate shunt, which is one of the objectives of the present invention, can be accomplished in a wide variety of microorganisms. The only requirement is that the genes controlling the glyoxylate shunt can be identified and mutated. In many cases, the most straightforward method for decreasing the flow of carbon through the glyoxylate shunt is to mutate one or more genes that encode for an enzyme of the glyoxylate shunt. However, any other method that accomplishes substantially the same result will also be an embodiment of the present invention. For example, in the yeast *Saccharomyces cerevisiae*, isocitrate lyase, and malate synthase are encoded by the genes ICL1 and ICL 2, and MLS1 and MLS 2 (DAR7) respectively, and glyoxylate shunt activity can be decreased by mutating one or more of those genes. Moreover, expression of ICL1 and MLS1 are positively regulated by the product of the FIL1 (RRF1) gene, so mutation of the FIL1 gene can also be used to decrease flow of carbon though the glyoxylate shunt in Saccharomyces and other yeasts (Kanai et al., 1998).

In the present invention, unique and advantageous combinations of gene mutations have been employed to direct the carbon flow to succinic acid production. In addition, the succinic acid production is coupled with microbial growth which in turn is coupled to cellular ATP level and redox balance.

The term "redox balance" refers to the ability of the cell to maintain the appropriate ratio of NADH to $NAD^+$. In other words, the cells are able to oxidize the NADH so that there is enough $NAD^+$ to oxidize the carbohydrate substrates during the anaerobic fermentative growth. During aerobic growth, the $NAD^+$ pool is regenerated through oxidative phosphorylation involving NADH. However, under anaerobic growth condition the regeneration of $NAD^+$ pool is achieved only by means of manipulating the flow of carbon through various metabolic pathways inside the cell which could oxidize NADH.

During the aerobic growth in the bacterial cells, the sugars transported into the cells are fully metabolized with the release of carbon dioxide. $NAD^+$ is consumed in the oxidation of carbon compounds with the resulting formation of NADH. The NADH thus formed is oxidized through oxidative phosphorylation with net consumption of oxygen and regeneration of $NAD^+$. On the other hand, when the bacterial strains are grown in anaerobic or microaerobic conditions, the sugar molecules are not fully metabolized. The intermediates of the glycolytic pathway and tricarboxylic acid cycle as well as the reducing power generated in the form of NADH are disposed off through a number of other carbon pathways that becomes operational under anaerobic or microaerobic conditions. As a result, under anaerobic or microaerobic conditions, the bacterial cells accumulate a number compounds which are found to be industrially valuable. The list of the industrial chemical compounds that can be obtained through bacterial fermentation process includes but not limited to succinate, malate, acetate, ethanol and lactate. One approach to produce a particular compound of interest under anaerobic or microaerobic condition using a bacterial strain is to facilitate the pathways leading to the production of that particular chemical entity while blocking the pathways for the synthesis of other compounds. Thus in the commercial production of succinic acid using bacterial biocatalysts, the pathways for the production of lactate, acetate and ethanol should be blocked.

The carbon flow to lactate occurs through two different routes. Pyruvate produced at the end of the glycolytic pathway is reduced by lactate dehydrogenase (ldhA) enzyme using NADH as a co-factor. Lactate is also derived from the methylglyoxal which in turn is derived form dihydroxyacetone phosphate. The enzyme mgsA is responsible for the production of methylglyoxal from dihydroxyacetone phosphate. Inactivation of the ldhA and msgA genes would block the pathways for the production of lactate. The inactivation of the ldhA, msgA or any other genes useful in the present invention is achieved by following one or other method well know in the field of microbial genetics. The inactivation of the microbial genes can be achieved through mutations leading to the alteration of the coding sequence, removal of the coding sequence for these proteins from the chromosomal DNA, insertion of an exogenous sequence in the middle of the open reading frame of genes, or other any other changes in the genes that would reduce the activity of the enzyme encoded by that particular gene. The deletion of the open reading frame of the gene without the introduction of any foreign DNA sequence is the preferred way of gene inactivation.

As is the case with the lactate production, the alcohol production is also dependent on the availability of pyruvate produced at the end of the glycolytic cycle. The enzyme alcohol dehydrogenase (adhE) reduces acetyl-CoA using the co-factor NADH to produce alcohol. Acetyl-CoA is derived from pyruvate either by the action of pyruvate dehydrogenase (pdh) or pyruvte formate lyase (pflB). Inactivation of pdh and pflB enzymes can be used to block the pathways for the production of alcohol.

Acetate is derived from the acetyl-CoA by the action of two different enzyme namely phosphate acetyltransferase (pta) and acetate kinase (ackA). Acetate is also produced directly from pyruvate by the action of pyruvate oxidase (poxB). Inactivation of the ackA, pta and poxB genes would block the flow of carbon to acetate. The ackA, pta and poxB genes can be inactivated by gene deletion, by insertional inactivation using an exogenous DNA sequence, by mutating the gene, or by using the antisense RNA.

In yet another embodiment of the present invention, the functional homologues of the genes involved in the fermentative pathway are also inactivated besides inactivating the genes well known to be involved in one or other fermentative pathway. A propionate kinase with acetate kinase activity is encoded by the tdcD gene which is produced only for the degradation of threonine. However, during the anaerobic growth with 10% (w/v) glucose, the expression of tdcD could functionally replace aockA. In addition, the adjacent tdcE gene in the same operon is similar to pflB and encodesoketobutryate formate lyase with pyruvate formate-lyase activity. In one aspect of the present invention, the tdcDE genes are inactivated to prevent the entry of carbon into fermentative pathway and to assure the flow of carbon into the TCA cycle.

A number of tricarboxylic acid intermediates also act as the branching point for the biosynthesis of amino acids. Aspartate aminotransferase (aspC) is a multifunctional enzyme that catalyzes the synthesis of aspartate, phenylalanine and other compounds by transamination. In this reaction, L-aspartate is synthesized from oxaloacetate by transamination with L-glutamate. Deleting the aspC gene could increase succinate production by reducing carbon flow into aspartate.

Besides blocking the pathways for the production of unwanted chemicals, it is also necessary to maintain the redox balance within the bacterial cell. The redox balance is determined by the relative ratio of $NAD^+$/NADH. $NAD^+$ and NADH are important cofactors in the functioning of a number of key enzymes in the central carbon metabolism. There is a limited pool of $NAD^+$ within the cell and reduction of the entire $NAD^+$ to NADH would have serious impact on the continuous flow of carbon through tricarboxylic acid cycle.

Succinic acid is an intermediate in the tricarboxylic acid cycle and it can be produced through three different routes revolving around the tricarboxylic acid cycle. Oxaloacetate is derived from the carboxylation of PEP by PEP carboxylase. The oxaloacetate molecule thus produced can be reduced to malate. Fumarate is produced from malate by dehydrogenation reaction catalyzed by fumarase enzyme. Fumarate is reduced to succinate by fumarate reductase. Thus the production of succinate from oxaloacetate requires two molecules of NADH for every molecule of succinate produced. This pathway from oxaloacetate to succinate is referred as reductive pathway for succinate production.

The glycolytic intermediates phosphoenol pyruvate (PEP) and pyruvic acid can be carboxylated to improve the carbon flow into the TCA cycle. Under normal conditions, the carbon entry into the TCA cycle is accomplished by the action of citrate synthase which combines the acetyl-CoA derived from pyruvate with oxaloacetate, an intermediate in TCA cycle, to produce citric acid. By means of improving the efficiency of one or more carboxylating enzymes present within the cell, it is possible to carboxylate phosphoenol pyruvate and pyruvate to oxaloacetate, a TCA cycle intermediate. The oxaloacetate thus produced from the carboxylating reaction can be further reduced through the reductive arm of the TCA cycle to produce succinic acid.

The present invention provides a method for manipulating the carboxylating enzymes present within the cell besides manipulating the flow of carbon through tricarboxylic acid cycle as a method to increase the succinic acid yield during anaerobic fermentative growth. It is well known in the art that by means of introducing pyruvate carboxylase (pyc) from an exogenous source it is possible to carboxylate pyruvate to oxaloacetic acid. Some microbial strains well suited for genetic manipulations such as *E. coli* do not have a pyc gene. A pyc genes derived from other bacterial species such as *Rhizopium elti* and *Lactobacillus lacti* can be introduced into the genetically modified *E. coli* strains to improve succinic acid production. Since the present invention is focused on manipulating the endogenous genetic material without introducing any exogenous genetic material, it is preferable to manipulate the endogenous carboxylating enzymes for improving the succinic acid yield.

Four different endogenous carboxylating enzymes are known in *E. coli*. Two of these enzymes are responsible for carboxylating phosphoenol pyruvate and two other enzymes are responsible for the carboxylation of pyruvate derived from phosphoenol pyruvate derived from the action of pyruvate kinase enzyme. The enzyme phosphoenol pyruvate carboxylase (ppc) carboxylates phosphoenol pyruvate to oxaloacetate which could enter into reductive arm of the TCA cycle to produce succinate. By means of selecting a suitable promoter, the PEP carboxylase enzyme could be over expressed to enhance the rate of production of oxaloacetate from PEP. A mutant form of PEP carboxylase obtained from *Sorghum vulgare* can also be used to achieve an increased rate of oxaloacetate production.

The second carboxylating enzyme phosphoenol pyruvate kinase (pck) also carboxylates phosphoenol pyruvate to produce oxaloacetate, but normally catalyzes the reverse reaction as it is not expressed in the presence of glucose. The two other carboxylating enzymes namely NADH-linked maleic enzyme (maeB) and the NADPH-linked maleic enzyme (maeA/sfcA) carboxylate pyruvic acid to malic acid. The maeB and sfcA enzymes carboxylates the pyruvate derived from phosphoenol pyruvate by the action of pyruvate kinase.

Any one of the four carboxylating enzymes present in the cell can be genetically manipulated to increase its enzymatic activity in order to improve the carbon flow from glycolytic cycle intermediates into the TCA cycle. Of the four native carboxylating enzymes present in *E. coli*, the PPC-catalyzed reaction is strongly favored. Energy contained in PEP is lost in this reaction with the release of inorganic phosphate. The other three carboxylating enzymes, namely pck, maeA and sfcA (maeB), are not expected to function during the fermentative growth using glucose as the substrate as these three carboxylating enzymes are repressed by glucose. However, the gluconeogenic PEP carboxykinase (pck) can be genetically manipulated to improve the flow of carbon into the TCA cycle.

Besides enhancing the conversion of PEP and pyruvate to oxaloacetate for facilitating the succinate production through reductive arm of the tricarboxylic acid, genetic manipulations can also be followed to increase the PEP pool within the cell by means of manipulating the transport of the sugars into the cell. In the wild type *E. coli*, the glucose uptake is mediated by phosphotransferase system (PTS). PTS is a multicomponent protein complex and is responsible for the transport of the glucose and other sugars across the cytoplasmic membrane. The transport of the glucose by PTS system is accompanied by the phosphorylation of glucose transported into the cell. The phosphorylation of each glucose molecule transported into the cell requires a molecule of PEP leading to the depletion of PEP pool within the cell. One way to overcome this depletion of PEP pool by PTS is to decrease the activity of a PTS by means of mutating a gene coding for a protein associated with PTS. PTS is reported to have four different protein components coded by four different genes namely ptsG, ptsH, ptsI, and crr. Either one of these four genes can be inactivated either by deletion or by inserting a foreign DNA sequence in the middle of the coding sequence. In *E. coli* and other bacterial strains, there are other sugar transporters besides PTS. Therefore, with the inactivation of PTS, the bacterial cell will be able to transport the required sugars through other transporter systems. Besides directly manipulating the structural proteins associated with PTS, the PTS function can also be altered through the manipulation of the genes coding for the proteins involved in the regulation of genes coding for the structural proteins associated with PTS.

A second route for the production of succinate in many microorganisms involves the oxidative TCA pathway. In the oxidative pathway for succinate production, oxaloacetate combines with the acetyl-CoA to produce citrate which isomerizes into isocitrate. Isocitrate upon oxidative decarboxylation yields 2-ketoglutrate which upon second decarboxylation reaction yields succinate. The list of the enzymes present in the oxidative pathway for the production of succinate includes, in the example of E. coli, isocitrate dehydrogenase (icd), citrate synthase (gltA), succinyl-CoA synthetase (sucD). Our effort to understand each of these enzymes through gene deletion has shown that all of these enzymes involved in the oxidative pathway for succinate production are found to be indispensable for the survival of our engineered E. coli.

The third route for fermentative succinic acid production is known as glyoxylate shunt. In this pathway for succinic acid production, a molecule of isocitrate is converted into a molecule of succinic acid and a molecule of glyoxylate. The glyoxylate molecule combines with a molecule of acetyl-CoA to produce a molecule of malate. Malate enters into the reductive arm of the tricarboxylic acid cycle and results in the production of succinic acid. The initial conversion of isocitrate into succinic acid and glyoxylate is catalyzed by the enzyme isocitrate lyase coded by the aceA gene. The second enzymatic reaction in glyoxylate cycle responsible for the synthesis of malate from glyoxylate and acetyl-CoA is carried out by the malate synthease enzyme coded by the aceB gene.

Three genes aceA, aceB, and aceK are in a single operon and the expression of all these three genes are under the control of the repressor protein encoded by iclR gene. Efforts have been made to relieve the repression of expression of aceBAK operon by means of deleting iclR gene. The purpose of the iclR gene deletion was to allow the over expression of the aceA leading to a functional glyoxylate shunt. It is generally considered that an operational glyoxylate shunt is essential to maintain the redox balance necessary to achieve the desirable levels of succinic acid production under fermentative conditions. Efforts have also been made to express the aceA gene under a constitutive promoter. Contrary to this expectation that an operational glyoxylate shunt is essential for succinate production, the results of the present invention have shown that the glyoxylate shunt is not a significant pathway for carbon flux to succinate in our engineered E. coli strains. The results of the present invention have shown that a deletion of gene encoding isocitrate lyase (aceA) and disruption of glyoxylate bypass pathway has no effect on glucose utilization or succinate production.

As shown by the results of the present invention, in engineering a microbial strain as a biocatalyst for succinic acid production, besides blocking the carbon flow from central metabolic pathway to acetate, lactate, ethanol and amino acid biosynthesis, the carbon flow through glyoxylate shunt can also be blocked without any impact either on the rate of succinic acid production or glucose utilization. A bacterial strain with one or more deletions in a gene coding for an enzymes involved in the glyoxylate shunt is useful in further genetic analysis of the relative contribution of the oxidative and reductive arms of the tricarboxylic acid cycle toward the fermentative succinic acid production and identifying further genetic manipulations necessary to increase the succinic acid production to approach the theoretical maximum limit. Availability of a bacterial strain where the carbon flow occurs only through two routes as opposed to the wild type bacterial strain where the carbon flow to succinic acid occurs through three different routes makes it easier to conduct further genetic analysis to achieve further improvements in succinic acid yield. Increasing the flow of the carbon either through the oxidative arm of the tricarboxylic acid cycle or through the reductive path of the tricarboxylic acid cycle in the absence of an operational glyoxylate shunt can be used as a means to further enhance the production rate or productivity of succinate from glucose. The carbon flow either through the oxidative arm of the tricarboxylic acid cycle or through the reductive arm of the tricarboxylic acid cycle can be achieved by enhancing the expression of the enzymes involved in the oxidative and reductive arm of the tricarboxylic acid cycle. Thus the enzymes involved in the oxidative arm of the tricarboxylic acid cycle such as citrate synthase (gltA), aconitase (acnA and acnB), isocitrate dehydrogenase (icd), α-ketoglutrate dehydrogenase and succinyl-CoA synthetase (sucC and sucD) can be over expressed to increase the succinic acid yield. Similarly, the enzymes participating in the reductive arm of the tricarboxylic acid cycle such as malate dehydrogenase (mdh), fumarase (fumA, fumB, and fumC), and fumarate reductase (frdA, B, C, D) can be over expressed to increase the succinic acid yield. These enzymes participating in the tricarboxyllic acid cycle can be over expressed either individually or in combination of two or more enzymes simultaneously.

A decrease in activity of the glyoxylate shunt can be achieved by inactivating either the aceA gene or aceB gene. It is also possible to achieve the disruption of glyoxylate shunt by means of inactivating both the aceA and aceB genes. The inactivation of the aceA and aceB genes can be done by any method that mutates or inactivates the gene including deleting the entire coding sequence of the gene or through inserting a foreign DNA sequence in the middle of the coding sequence. Inactivation of the gene expression by means of deleting the coding sequence without introducing any exogenous sequence is the preferred method.

The aceA and aceB genes can be deleted first in a bacterial strain selected for succinic acid production followed by the other genetic modifications known to facilitate succinic acid production in a commercial scale. The secondary genetic modifications include blocking the carbon flow to ethanol, acetate, lactate and amino acids. Alternatively the aceA and aceB gene deletions can be introduced into the bacterial strains already genetically modified to produce succinic acid in significant quantities. For example, the aceA or aceB gene deletions can be introduced into the E. coli strain KJ122 described in the PCT Patent Application Nos. WO 2008/021141 and WO 2010/115067. The bacterial strains thus engineered to have deletions in the genes functional in the glyoxylate shunt produce at least 1 mol of succinic acid per mol of glucose utilized.

It was not possible to delete any of the following TCA cycle genes from strain KJ122: icd, encoding isocitrate dehydrogenase; gltA, encoding citrate synthase; and sucD, encoding succinyl-CoA synthetase. Similarly deletion of the iclR, encoding the repressor of the aceBAK operon has no effect on growth of E. coli strain or the production of succinic acid in minimal medium containing glucose under microaerobic conditions.

EXPERIMENTAL SECTION

General Remarks

Strain and inoculum preparations: *E. coli* strain KJ122 (*E. coli* C, ΔldhA, ΔadhE, ΔackA, ΔfocA-pflB, ΔmgsA, ΔpoxB, ΔtdcDE, ΔcitF, ΔaspC, ΔsfcA) was used as an example in the present invention. KJ122 was derived from *E. Coli* C (ATCC 8739) strain through genetic modifications as described by Jantama et at (2008a; 2008b) and in the International Patent Applications published under Patent Cooperation Treaty with International Publication Nos. WO 2008/115958 and WO 2010/115067. All these documents are incorporated herein by reference.

*E. coli* strain KJ122 is capable of fermenting 10% glucose in AM1 medium to produce about 60 g/L succinate, in about 72 to 100 hours. AM1 medium is a minimal glucose medium containing 2.63 g/L $(NH_4)_2HPO_4$, 0.87 g/L $NH_4H_2PO_4$, 1.5 mM $MgSO_4$, 1.0 mM betaine, and 1.5 ml/L trace elements. The trace elements are prepared as a 1000× stock and contained the following components: 1.6 g/L $FeCl_3$, 0.2 g/L $CoCl_2.6H_2O$, 0.1 g/L $CuCl_2$, 0.2 g/L $ZnCl_2.4H_2O$, 0.2 g/L $NaMoO_4$, 0.05 g/L $H_3BO_3$, and 0.33 g/L $MnCl_2.4H_2O$. The pH of the fermentation broth is maintained at 7.0 by feeding a solution containing 1.2N KOH, plus 2.4 M $K_2CO_3$ as needed.

Cell growth: Cell mass was estimated by measuring the optical density at 550 nm ($OD_{550}$) using a Thermo Electronic Spectronic 20 spectrophotometer.

Organic acid and sugar analysis: The concentration of various organic acids and sugars were measured by HPLC. Succinic acid and other organic acids present in the fermentation broth were analyzed on Agilent 1200 HPLC apparatus with BioRad Aminex HPX-87H column. BioRad Microguard Cation $H^+$ was used as a guard column. The standards for HPLC analysis were prepared in 0.008N sulfuric acid. The HPLC column temperature was maintained at 50° C. Sulfuric acid at 0.008N concentration was used as a mobile phase at the flow rate of 0.6 ml/min. Quantification of various components was done by measuring their absorption at 210 nm.

Example 1

Deletion of aceA Gene in KJ122 Strain

In this invention the aceA gene was deleted from the KJ122 strain. International Patent Applications published under Patent Cooperation Treaty Nos. WO 2008/115958 and WO 2010/115067 describe the genetic changes that have been introduced in the KJ122 strain. The already existing genetic modifications in KJ122 strain of *E. coli* include blocking the carbon flow to ethanol, acetate, formate, and lactate. In deleting the aceA gene from KJ122 strain, a two-step homologous recombination process also called a two step gene replacement method, described in detail in the International Patent Application published under Patent Cooperation Treaty with Nos. WO 2008/115958 and No. WO 2010/115067 and in Thompson et al (2005) was followed. With this method, no antibiotic genes or scar sequences remain on the chromosome after gene deletion.

In the first recombination, part of the target gene is replaced by a DNA cassette containing a chloramphenicol resistance gene (cat) and a levansucrase gene (sacB). In the second recombination, the cat-sacB cassette is replaced with native sequences omitting the region of deletion. Cells containing the sacB gene accumulate levan during incubation with sucrose and are killed. Surviving recombinants are highly enriched for loss of the cat-sacB cassette.

In this invention, in the first stage cat-sacB cassette was amplified using NheI cut plasmid pLOI4151 (SEQ ID NO. 9) and the primer sets SD131 and SD132. The first 50 nucleotides in SD131 primer corresponds to the 50 nucleotide sequences immediately upstream of ATG codon of aceA gene. The rest of the nucleotides in this primer correspond to the sequence of cat region in the cat-sacB cassette. The first 50 nucleotides in SD132 primer corresponds to the 50 nucleotide sequences immediately downstream of stop codon for accA gene. The rest of the nucleotide sequence in this primer contained the nucleotide sequence corresponding to sacB region of the cat-sacB cassette.

The PCR product derived from the reaction using this primer set (SD131/SD132) was used in the transformation of KJ122 strain containing λ, Red recombinase plasmid pKD46 expressing Red recombinase for high recombination. pKD46 is described in Datsenko and Wanner (2000), and is available from the *Coli* Genetic Stock Center, Yale University, New Haven, Conn., USA. The transformants were selected on the chloramphenicol containing medium. Two different colonies (SD187 and SD188) were selected on the chloramphenicol medium.

Due to the efforts in primer designing, in the SD 187 and SD 190 strains, the cat-sacB cassette precisely replaced the open reading frame of aceA. During the second transformation, the specifically designed primer dimer precisely removed the cat-sacB cassette from the chromosome of the SD187 and SD190 strains resulting in the strains SD 193 and SD 195 respectively. The strains SD 193 and SD 195 contain precise deletion in the open reading frame of the aceA gene.

Example 2

Measurement of Glucose Utilization and Succinic Acid Production

*E. coli* strains KJ122, SD187, SD190, SD193 and SD195 were grown in AM1 medium containing 10% glucose. AMl medium contains 2.63 g/L $(NH_4)_2HPO_4$, 0.87 g/L $NH_4H_2PO_4$, 1.5 mM $MgSO_4$, 1.0 mM betaine, and 1.5 ml/L trace elements. The trace elements are prepared as a 1000× stock and contained the following components: 1.6 g/L $FeCl_3$, 0.2 g/L $CoCl_2.6H_2O$, 0.1 g/L $CuCl_2$, 0.2 g/L $ZnCl_2.4H_2O$, 0.2 g/L $NaMbO_4$, 0.05 g/L $H_3BO_3$, and 0.33 g/L $MnCl_2.4H_2O$. The pH of the fermentation broth is maintained at 7.0 with: 1:4 (6 N KOH: 3 M $K_2CO_3$) (1.2N KOH, 2.4 M $K_2CO_3$).

Fermentations were started by streaking on a LB plate a glycerol stock of *E. coli* strain genetically engineered to produce Succinic acid and stored in the −80° C. freezer. After 16 hours of growth at 37° C., cells from the plate were scraped off and inoculated into sterile glass tubes containing 5 ml of NBS minimal medium containing 2% glucose and grown overnight at 37° C. with rotation. This entire culture was used to inoculate shake flasks containing 50 ml NBS medium with 2% glucose and 0.5% corn steep liquor and grown at 37° C. overnight with shaking at 150 rpm. This shake flask grown inoculum was used to inoculate fermentation vessel containing 300 ml AM1 medium with 10% glucose, 1 mM betaine and 0.03M $KHCO_3$. Fleaker fermentation vessels are small fermentation vessels with a total volume capacity of 500 ml and usual starting media volume of 300 ml. Fleakers have automated pH control and the fermenting culture is maintained at pH 7.0 by automated neutralization with a base mixture consisting of 6 N KOH and 3 M $K_2CO_3$. The fleaker fermentations were maintained at a pH of 7.0, 37° C. with 150 rpm stirring.

Cell mass was estimated by measuring the optical density at 550 nm ($OD_{550}$) using a Thermo Electronic Spectronic 20 spectrophotometer.

Figure 2:
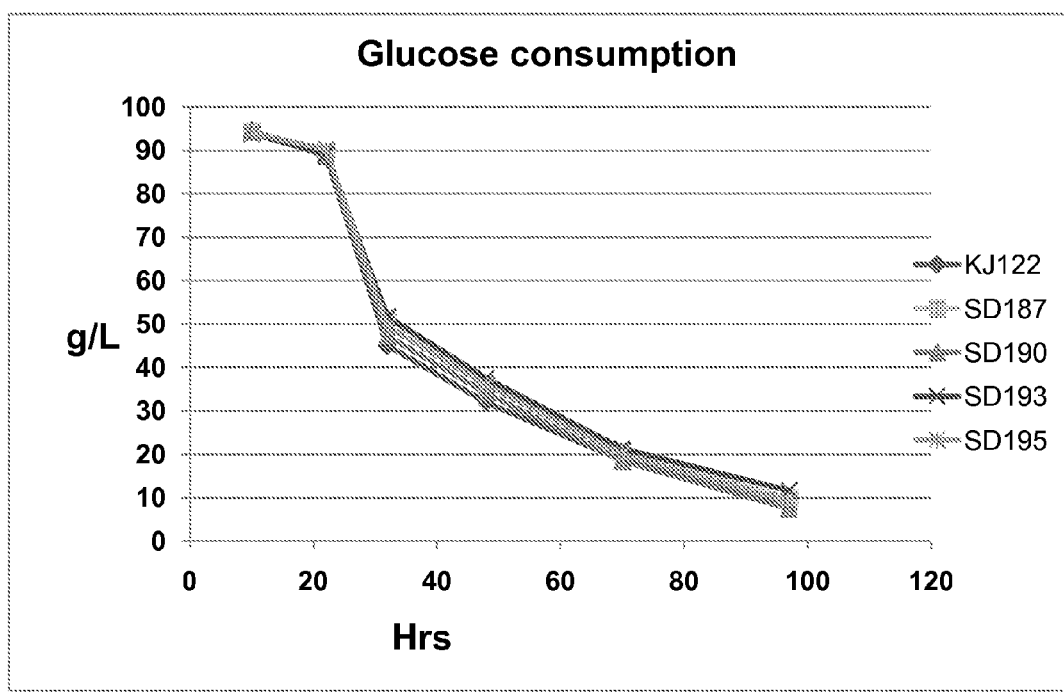
FIG. 2. Glucose consumption curves for KJ122, SD187, SD190, SD193, and SD195 strains of $E.\ coli$. The bacterial strains were grown under microaerobic conditions in a fermentor in a mininal medium with 10% glucose. During the course of 100 hours, glucose concentration in the fermentor was measured at specific time points. The values on the y-axis are the grams of glucose per liter of culture medium.
Figure 3:
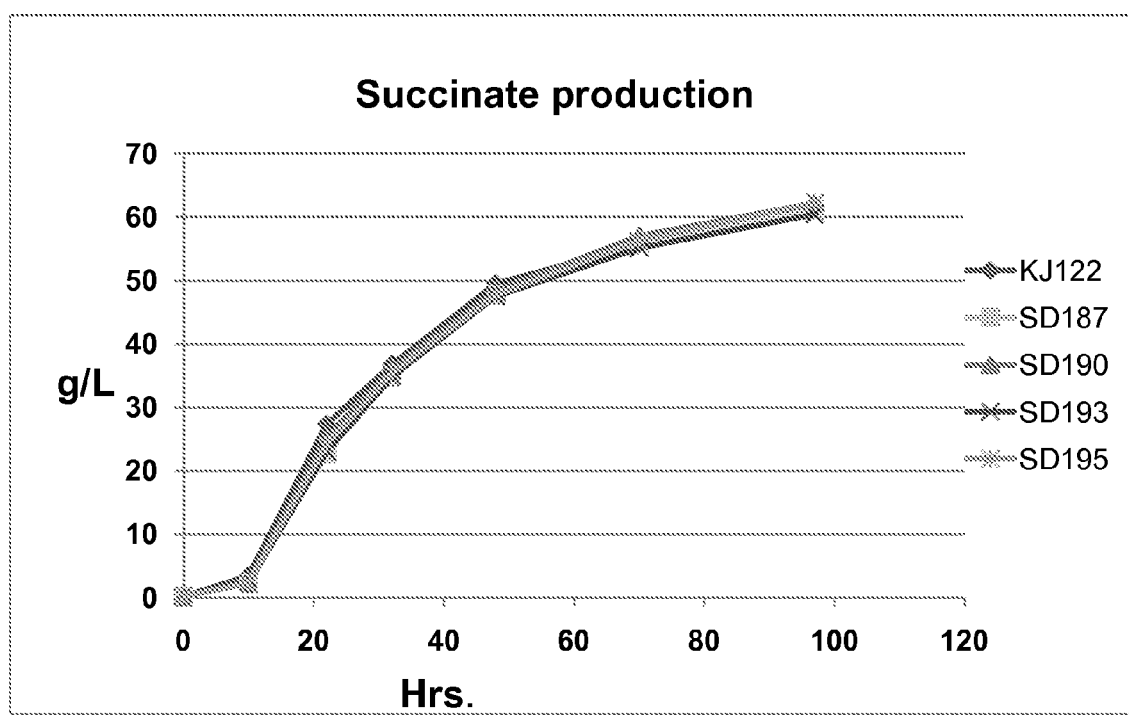
FIG. 3. Succinic acid production curves by KJ122, SD187, SD190, SD193, and SD195 strains of $E.\ coli$. The bacterial strains were grown under anaerobic condition in a fermentor in a minimal medium with 10% glucose. During the course of 100 hours, succinic acid concentration in the fermentor was measured at specific time points. The values on the y-axis are the grams of succinic acid per liter of culture medium.

FIG. 2 provides fermentation profile of glucose consumption by KJ122, SD187, SD190, SD193, and SD195 strains. As shown in the FIG. 2, all the strains showed a similar pattern for glucose utilization. At 100 hours after the start of the fermentation only 10% of the original glucose content remained in the medium. FIG. 3 shows the profile for succinic acid production in KJ122, SD187, SD190, SD193, and SD195 strains. As the results indicate all the five strains used in this study, showed a similar profile for succinic acid production suggesting that the deletion of aceA gene does not have any negative impact on the succinic acid production. At the end of 100 hours of fermentation, the succinic acid yield in all the strains were found to be about 60 g/L. This result was surprising, since in a prior art disclosure, the highest succinate yield was obtained from the strain with the highest isocitrate lyase activity (Vemuri, 2002a).

Example 3

Deletion of the iclR Gene in Strain KJ122

The iclR gene encodes a repressor of the glyoxylate shunt genes, aceB,A, and K in wild type *E. coli* strains. Deletion of the iclR gene in KJ122 was accomplished by transduction using the generalized transduction phage P1 vir (Silhavy et al., (1984) Experiments With Gene Fusions, Cold Spring Harbor Laboratory Press, Cold Spring Harbor, N.Y., pp 107-112). The donor strain was JW 3978-2 (ΔiclR785::kan), available from the *Coli* Genetic Stock Center, Yale University, New Haven, Conn., USA. The recipient strain was KJ122, and the selection was for resistance to kanamycin sulfate at 50 mg/l in rich medium (LB) plates. The resulting strain, named RY847B, was tested in small scale fermentors as described above in Example 2 for succinate production from glucose. Deletion of iclR had almost no effect on initial growth rate or succinate titer, and if anything, the deletion decreased the growth rate and titer slightly. This result was surprising, since in the prior art, it is disclosed that deletion of iclR increased succinate production (Sanchez et al., 2005; Wang et al., 2006).

Example 4

Theoretical Yield of ATP from the Glyoxylate Shunt Compared to the Oxidative TCA Pathway Given the surprising results of the previous examples, the inventors sought a rational explanation for the results. In theory, for a microorganism to produce succinate from glucose in an anaerobic or microaerobic fermentation, redox balance can be achieved either by running a combination of the reductive TCA pathway and the glyoxylate shunt, or by a combination of the reductive TCA pathway and the oxidative TCA pathway (see FIG. 4 for the theoretical stoichiometries). However, the ATP yield is higher for the combination that uses the oxidative TCA pathway (18 ATP for the oxidative TCA combination compared to 14 ATP for the glyoxylate shunt combination). Given that anaerobic or microaerobic conditions generally result in low ATP yield, this difference is important. The conclusion here is that the oxidative TCA pathway is equally effective as the glyoxylate shunt in achieving redox balance, but the oxidative TCA pathway gives a higher for yield of ATP than the glyoxylate shunt.

Given that the beginning and ending compounds for the two possible redox balance pathways in this example are identical (glucose and succinate), and since the yield of ATP is higher for the oxidative TCA pathway, the oxidative TCA pathway must be less favorable thermodynamically. In other words, if all other parameters are held constant, the overall thermodynamic equilibrium between glucose and succinate would be higher (in favor of glucose) for the oxidative TCA pathway. As such, if the glyoxylate shunt enzymes are present, then carbon would be expected to flow through the glyoxylate shunt in preference to the oxidative TCA pathway, even though the conservation of energy in the form of ATP is not as favorable. Thus, in order to conserve ATP, it is useful to force the cell to use the oxidative TCA pathway by decreasing or eliminating one or more enzymes of the glyoxylate shunt and by decreasing or eliminating the phosphorylation of IDH.

According to the stoichiometries shown in FIG. 4, in a redox balanced state, two out of 12 succinate molecules (about 17%) are derived from either the glyoxylate shunt or the oxidative TCA pathway, and the remaining 83% would be derived from the reductive TCA pathway. However, those stoichiometries only take into account the conversion of glucose to succinate. In a real cell, biosynthesis of cell mass will influence the fraction of succinate derived from the various pathways, so the actual flux through the oxidative TCA pathway will not be exactly 17%. In a strain where 5% or more of the succinate is derived from the oxidative TCA pathway, there should be sufficient conservation of ATP to give a significant and useful improvement in growth or efficiency of succinate production.

A strain for which the glyoxylate pathway has been eliminated (for example by deleting one or more genes for glyoxylate shunt enzymes) for all practical purposes will not produce any significant amount of succinate through the glyoxylate shunt pathway. If a parent strain grows on acetate as the sole carbon source, a derivative strain can be tested for elimination of the glyoxylate shunt pathway by checking for aerobic growth on a minimal medium, similar to AM1, described above, except that the glucose has been replaced with 50 mM potassium acetate as the sole carbon source, and the medium is buffered with 0.1 M MOPS (available from Sigma-Aldrich) and adjusted to a final pH of 7.0 with potassium hydroxide. If the derivative strain no longer grows significantly on acetate as the sole carbon source, then the glyoxylate shunt has been substantially eliminated. Alternatively, a derivative strain a can be tested for aerobic growth on a fatty acid as the sole carbon source on a medium similar to that described above, but where the only carbon source is 1 g/l of a fatty acid, such as stearic acid, and the medium is adjusted to a final pH of 7.0 with potassium hydroxide.

In practice, it might be difficult to accurately measure the percent of succinate that is derived from the oxidative TCA pathway. As such, for the purposes of this invention, any strain that becomes unable to grow aerobically on minimal acetate medium due to one or more mutations that decrease activity of the glyoxylate shunt will be considered to derive 5% or more of its succinate from the oxidative TCA pathway anaerobically or microaerobically from glucose or other sugar.

As mentioned above, succinate producing strains of the prior art use the glyoxylate shunt, and the oxidative TCA is presumably not being used because 2-ketoglutarate dehydrogenase "is virtually absent". The present inventors have discovered that strain K122 must be using the oxidative TCA pathway, because 1) elimination of the glyoxylate shunt did not decrease growth or succinate production, 2) elimination of iclR did not increase growth or succinate production, and 3) deletion of any one of several genes of the oxidative TCA pathway appeared to be a lethal event. Clearly, the regulation of the level of activity of 2-ketoglutarate dehydrogenase and/or the genes that encode the subunits of 2-ketoglutarate dehydrogenase (sucA, sucB, and lpd), and possibly the regulation of other enzymes and genes encoding of the oxidative TCA pathway, is fundamentally different in KJ122 compared to other prior art succinate producing strains. Under anaerobic or microaerobic conditions, the oxidative TCA pathway enzymes and/or genes must be increased in activity compared to other prior art succinate producing strains.

Strain KJ122 already uses the oxidative TCA pathway, but this strain can be made more stable genetically by deleting genes of the glyoxylate shunt. Moreover, construction of future succinate producing strains can have deletion of the glyoxylate shunt built in, to force the cells to use the ATP conserving oxidative TCA pathway.

Although the examples given herein refer specifically to succinic acid production in *E. coli*, the principles elaborated herein can be applied to a wide variety of microorganisms, the only limitation being that the organism must be amenable to classical genetic modification or genetic engineering. This group of amenable microorganisms includes many bacteria, archeons, yeasts, filamentous fungi, algae, dinoflagellates, and diatoms. For example, in the yeast *Saccharomyces cerevisiae*, mutation of one or more of ICL1, ICL2, MLS1, or MLS2 would accomplish the same purpose as deletion of one or more of aceA, aceB, or aceK in *E. coli*.

One embodiment of the present invention is a microorganism that "uses the oxidative TCA pathway for attaining redox balance for anaerobic or microaerobic organic acid biosynthesis", for example succinic acid biosynthesis. A microorganism can be shown to be in this category by any one of several genetic methods that are well known in the art. In the first set of methods, an attempt is made to remove the activity of one of the steps in the oxidative TCA pathway, for example by deleting a gene that codes for one of the enzymes in the pathway, for example the gene encoding isocitrate dehydrogenase, which in *E. coli* is the icd gene. If the deletion attempt is unsuccessful for the strain in question under a set of growth conditions, and control experiments are done to rule out technical problems with the attempted construction, then it can be concluded that the gene and its function is essential under those growth conditions, and therefore that the microorganism uses the oxidative TCA pathway.

For example, the icd gene can be deleted from a wild type *E. coli* K-12 strain, and one of the Keio collection deletion strains, JW 3978-2 (ΔiclR785::kan), available from the *Coli* Genetic Stock Center, Yale University, New Haven, Conn., USA, is just such a strain. A P1 vir lysate is made on that strain as a donor, and the donor lysate is used to transduce two different strains to kanamycin resistance on LB plates containing 50 mg/l kanamycin sulfate. The first recipient strain is the strain in question, for example KJ122. The second strain is the wild type ancestor of KJ122, which is wild type *E. coli* C. If transductants are not obtained from KJ122, but are obtained from *E. coli* C, then it has been shown that the donor lysate is functional, that is, it contains transducing particles of the desired type. A second control is done to show that both recipient strains are functional, that is, competent to be transduced. This second control is done by making a P1 vir lysate on strain JW 0073 (also available from the *Coli* Genetic Stock Center), which carries a ΔleuA::kan insertion. Since leuA is not directly involved with the oxidative TCA pathway, it can be easily deleted from both KJ122 and *E. coli* C, selecting on the same LB kanamycin plates as used above, showing that the recipient strains are both competent for transduction.

A more formal proof that a gene is essential can be obtained by constructing a merodiploid, and showing that the deletion construct can integrate into one of the two copies of the gene in a merodiploid. Another method is to isolate a temperature sensitive mutant that has a mutation in the gene in question, and show that growth ceases at the non-permissive temperature under the growth conditions of interest. Yet another method is to place the gene in question on a plasmid that has a temperature sensitive replication origin, and then delete the gene from the chromosome. The resulting strain will then be temperature sensitive for growth under the growth conditions of interest, for example, anaerobic or microaerobic in a minimal medium.

In the yeast *Saccharomyces cerevisiae*, a gene can de shown to be essential in a haploid strain by a method similar to that described above for *E. coli*, except that attempting the deletion is done by transformation with linear DNA containing the deletion and ends homologous to the target gene, instead of by transduction. Another well known method to show a gene is essential in *S. cerevisiae* is by deleting one of the two copies of said gene in a diploid strain. The diploid strain containing the desired deletion is then sporulated, and the tetrads are dissected. If only two out of four spores for several different tetrads can grow under conditions of interest, then it can be concluded that the gene is essential, since two of the four spores will gave generally have received the deletion, while the other two will have receive the wild type allele. For some enzymes in yeast, there are two or more functional genes per haploid genome. In that case deletion of all genes that code for the enzyme in question might have to be done, but the principle is the same. For example, *S. cerevisiae* contains three different genes encoding three different isozymes of isocitrate dehydrogenase, encoded by IDP1, IDP2, and IDP3. If all three genes are functional under a set of growth conditions of interest, then one would have to attempt to delete all three genes from a haploid to determine whether isocitrate dehydrogenase is essential under a condition of interest. Again, appropriate control would be done to eliminate the possibility of technical problems.

A second set of methods for determining whether a microorganism that "uses the oxidative TCA pathway for attaining redox balance for anaerobic or microaerobic organic acid biosynthesis" is to remove, for example by one or more gene deletions, substatially all activity of one of the glyoxylate shunt enzymes, such as isocitrate lyase, using methods analogous to those described above. If the resulting strain still grows and produces an organic acid of interest, such as succinic acid, then it can be concluded that the microorganism in question "uses the oxidative TCA pathway for attaining redox balance for anaerobic or microaerobic organic acid biosynthesis", because the glyoxylate shunt would have been shown to be dispensable.

The applicants' invention has been described in detail above with particular reference to preferred embodiments. A skilled practitioner familiar with the above detailed description can make any modification without departing from the spirit of the claims that follow.

TABLE 1

Primer sequences and bacterial strains

Primers

| Primer No./Name | Primer Sequence |
| --- | --- |
| SEQ ID NO. 1/SD131 | 5'ttcctgaccctgccaggctaccgcctgttagcgtaaaccaccacataacttgtgacggaagatcacttcg3'. |
| SEQ ID NO. 2/SD132 | 5'tgcggcgtgaacgccttatccggcctacagtcagcaacggttgttgttgcataagaaataaaagaaaatgccaataggatatcggcattttcttttgcgttttt 3'. |
| SEQ ID NO. 3/SD133 | 5'ttgatttcctgaccctgccaggctaccgcctgttagcgtaaaccaccacataactgcaacaacaacgtt3' |
| SEQ ID NO. 4/SD134 | 5'ccggatgcggcgtgaacgccttatccggcctacagtcagcaacggttgttgttgcagttatgtggtggtt3' |
| SEQ ID NO. 5/SD58 | 5'gccgatatcctattggcatt3' |
| SEQ ID NO. 6/SD135 | 5'accacttccgatgagttaattg3' |
| SEQ ID NO. 7/SD136 | 5'ctcatcaggagcagagaattgc3' |
| SEQ ID NO. 8/SD137 | 5'gtttctcccaggggcgtttt3' |

Bacterial strains

| Bacterial strain | Genotype | Description |
| --- | --- | --- |
| SD187 | KJ122, cat-sacB@ aceA + pKD46 | cat-sacB cassette (made with primers SD131/132) replacing the exact aceA ORF. Stage 1 Clone during precise aceA deletion clone #7 + pKD46, $Cm^R$. Sucrose $^S$, $Amp^R$ sacB integration tested by PCR (PCR Primers SD58/136) |
| SD190 | KJ122, cat-sacB@ aceA + pKD46 | cat-sacB cassette (made with primers SD131/132) replacing the exact aceA ORF. Stage 1 Clone during precise aceA deletion clone #23 + pKD46, $Cm^R$. $Sucrose^S$, $Amp^R$ sacB integration tested by PCR (PCR Primers SD58/136) |
| SD193 | KJ122 ΔaceA | Obtained by removing cat-sacB cassette from stage 1 clone 7 (SD187) using PCR dimer product of primers SD133/134. Stage 2 Clone # 13 $Cm^S$, $Sucrose^R$, Tested by PCR (Primer pairs SD135/136 and SD136/137) |
| SD195 | KJ122 ΔaceA | Obtained by removing cat-sacB cassette from stage 1 clone 7 (SD187) using PCR dimer product of primers SD133/134. Stage 2 Clone # 13 $Cm^S$, $Sucrose^R$, Tested by PCR (Primer pairs SD135/136 and SD136/137) |

REFERENCES

All references are listed for the convenience of the reader. Each reference is incorporated by reference in its entirety.

U.S. Pat. No. 6,455,284
U.S. Pat. No. 7,223,567
U.S. Pat. No. 7,244,610
U.S. Pat. No. 7,262,046
U.S. Pat. No. 7,629,162
U.S. Pat. No. 7,790,416
U.S. Patent Application Publication No. 2006/0037577
U.S. Patent Application Publication No. 2006/0073577
U.S. Patent Application Publication No. 2007/0015261
U.S. Patent Application Publication No. 2009/0148914
International Patent Application Publication No. WO 2008/115958
International Patent Application Publication No. WO 2009/065718
International Patent Application Publication No. WO 2009/065777
International Patent Application Publication No. WO 2009/065718
International Patent Application Publication No. WO 2009/065777
International Patent Application Publication No. WO 2010/115067
Causey, T. B., Shamugam, K. T., Yomano, L. P., Ingram, L. O. (2004) "Engineering *Escherichia coli* for efficient conversion of glucose to pyruvate." *Proc Natl Acad Sci USA* 101:2235-2240.
Cronan, J., Laporte, D. (1996) "Tricarboxylic acid cycle and glyoxylate bypass" in *Escherichia Coli* and *Salmonella*." editors Neidhardt, F., et al., ASM Press, Washington, D.C., USA.
Datsenko, K. A., Wanner, B. L. (2000) "One-step inactivation of chromosomal genes in *Escherichia coli* K-12 using PCR products." *Proc Natl Acad Sci USA* 97: 6640-6645.
Deutscher, J., Francke, C., Postma, P. W. (2006) "How phosphotransferase system-related protein phosphorylation regulates carbohydrate metabolism in bacteria." *Microbio Mol Bio Rev* 70:939-1031.
Jansen, M., Fleminglaan, A., Verwaal, R., Wu, L., Sequeilha, L., Perkins, J. (2010) "Breakthrough technology for fermentative succinic acid production." Poster C25, Metabolic Engineering VIII, Engineering Conferences International, 32 Broadway, Suite 314, New York, N.Y. 10004, USA Jantama, K., Haupt, M. J., Svoronos, S. A., Zhang, X., Moore, J. C., Shanmugham, K. T., Ingram, L. O. (2008a) "Combining metabolic engineering and metabolic evolutions to develop nonrecombinant strains of Escherichia coli C that produce succinate and malate." Biotechnol Bioeng 99: 1140-1153.

Jantama, K., Zhang, X., Moore, J. C., Shanmugam, K. T., Svoronos, S. A., Ingram, L. O. (2008b)"Eliminating side products and increasing succinate yields in engineered strains of Escherichia coli C." Biotechnol Bioeng 101: 881-893.

Kanai T, Takeshita S, Atomi H, Umemura K, Ueda M, Tanaka A. (1998) "A regulatory factor Fil 1p, involved in derepression of the isocitrate lyase gene in Saccharomyces cerevisiae—a possible mitochondrial protein necessary for protein synthesis in mitochondria." Eur J Biochem. 256:212-20).

Lee, S. J., Lee, D-Y., Kim, T. Y., Kim, B. H., Lee J., Lee, S. Y. (2005) "Metabolilc Engineering of Escherichia coli for enhanced production of succinic acid, based on genome comparison and in silico gene knockout stimulation." App Environ Microbiol 71: 7880-7887.

Lin, H, Bennett, G. N., San, K. Y. (2005) "Metabolic engineering of aerobic succinate production systems in Escherichia coli to improve process productivity and achieve the maximum theoretical succinate yield." Metab Eng 7: 116-127.

Lin, H., Bennett, G. N., San, K. Y. (2005) "Genetic reconstruction of the aerobic central metabolism in Escherichia coli for the absolute aerobic production of succinate." Biotechnol Bioeng 89: 148-156.

Martinez, I., Bennett, G. N., San, K. Y. (2010) "Metabolic impact of the level of aeration during cell growth on anerobic succinate production by an engineered E. coli strain," Metabolic Engineering 12: 499-509.

Sanchez, A. M., Bennett, G. N., San K. Y. (2005) "Novel pathway engineering design of the anaerobic central metabolic pathway in Escherichia coli to increase succinate yield and productivity." Metab Eng 7: 229-239.

Silhavy, T., Berman, M., Enquist, L. (1984) "Experiments With Gene Fusions." Cold Spring Harbor Laboratory Press, Cold Spring Harbor, N.Y., pp 107-112.

Vemuri, G. N., Eiteman, M. A., Altman, E. (2002a) "Effects of growth mode and pyruvate carboxylase on succinic acid production by metabolically engineered strains of Escherichia coli." App Env Microbio 68: 1715-1727.

Vemuri, G. N., Eiteman, M. A., Altman, E. (2002b) "Succinate production in dual-phase Escherichia coli fermentations depends on the time of transition from aerobic conditions." J Ind Microbiol Biotech 28: 325-332.

Vemuri, G. N., Altman, E., Sangurdekar, D. P., Khodursky, A. B., Eiteman, M. A. (2006) "Overflow metabolism in Escherichia coli during steady-state growth transcriptional regulation and effect of the redox ratio." App Environ Microbiol 72: 3653-3661.

Vemuri, G. N., Eiteman, M. A., Olsson, L., Nielson, J. (2007) "Increasing NADH oxidation reduces overflow metabolism in Saccharomyces cerevisiae." Proc Natl Acad Sci USA 104: 2402-2407.

Wang, Q. et al., (2006) "Genome scale in silico aided metabolic analysis and flux comparisons of E. coli to improve succinate production." App Gen Mol Biotechnol 73: 887-894

Wu, H., Li, Z., Zhou, L., Ye, Q. (2007) "Improved succinic acid production in the anaerobic culture of an Escherichia coli pflB ldhA double mutant as a result of enhanced anapleurotic activities in the preceding aerobic culture." App Env Microbiol 73: 7837-7843, Zhang, X., Jantama, K., Moore, J. C., Jarboe, L. R., Shanmugam, K. T., Ingram, L. O. (2009) "Metabolic evolution of energy-conserving pathways for succinate production in Escherichia coli." Proc Natl Acad Sci USA 106: 20180-20185.

We claim:

1. A nonnaturally occurring *Escherichia coli* bacterium that produces at least 1 mole of succinate per mole of glucose, comprising a mutation that inactivates at least one of the gene selected from a group consisting of genes that encode isocitrate lyase, malate synthase and isocitrate dehydrogenase kinase.

2. The nonnaturally occurring *Escherichia coli* bacterium of claim 1, wherein said *Escherichia coli* bacterium further comprises a recombinant nucleic acid construct to over express one or more genes selected from a group consisting of genes that encode malate dehydrogenase, citrate synthase, aconitase, isocitrate dehydrogenase, α-ketoglutarate dehydrogenase, succinyl CoA synthetase, fumarase and fumarate reductase.

3. The nonnaturally occurring *Escherichia coli* bacterium of claim 1, further comprising a mutation that decreases the activity of a phosphoenol pyruvate-dependent phosphotransferase system.

4. The nonnaturally occurring *Escherichia coli* bacterium of claim 3, wherein the said mutation is in a gene selected from a group consisting of genes that encode PtsG, PtsI, PtsH and Crr proteins associated with a phosphoenol pyruvate-dependent phosphotransferase system for glucose transport.

5. The nonnaturally occurring *Escherichia coli* bacterium of claim 1, further comprising:
   a. a mutation that decreases the activity of a phosphoenol pyruvate dependent phosphotransferase system; and
   b. at least one mutation that increases the expression of one or more genes encoding a non-PTS sugar transporter.

6. The nonnaturally occurring *Escherichia coli* bacterium of claim 5, wherein said non-PTS sugar transporter is an ATP binding cassette transporter.

7. The nonnaturally occurring *Escherichia coli* bacterium of claim 5, wherein said non-PTS sugar transporter is a symporter.

8. The nonnaturally occurring *Escherichia coli* bacterium of claim 1, further comprising a mutation that inactivates at least one of the genes selected from a group consisting of genes that encode enzymes active as alcohol dehydrogenase, lactate dehydrogenase, pyruvate formate lyase, phosphotransacetylase, acetate kinase, pyruvate dehydrogenase, propionate kinase with acetate kinase activity, methylglyoxylate synthase, aspartate transaminase and pyruvate oxidase.

9. The nonnaturally occurring *Escherichia coli* bacterium of claim 1, further comprising a mutation that increases the expression of at least one of the genes selected from a group consisting of citrate synthase, aconitase, isocitrate dehydrogenase, α-ketoglutarate dehydrogenase, succinyl-CoA synthetase, malate dehydrogenase, fumarase, and fumarate reductase.

10. The nonnaturally occurring *Escherichia coli* bacterium of claim 1, further comprising a mutation in at least one of the genes associated with reductive path of a TCA cycle selected from a group consisting of genes that encode malate dehydrogenase, fumarase and fumarate reductase, wherein the mutation results in increased activity of the protein coded by the mutated gene.

11. The nonnaturally occurring *Escherichia coli* bacterium of claim 1, further comprising a mutation in at least one of the genes associated with oxidative path of a TCA cycle selected from a group consisting of citrate synthase, aconitase, isocitrate dehydrogenase, α-ketoglutaratedehydrogenase and succinyl-CoA synthetase, wherein the mutation results in increased activity of the protein coded by the mutated gene.

12. The nonnaturally occurring *Escherichia coli* bacterium of claim 1 further comprising a mutation that increases the expression of one or more genes selected from a group consisting of genes that encode phosphoenolpyruvate carboxylase, NADH dependent malic enzyme and NADPH dependent malic enzyme.

13. The nonnaturally occurring *Escherichia coli* bacterium of claim 1 further comprising an exogenous pyruvate carboxylase.

14. The nonnaturally occurring *Escherichia coli* bacterium of claim 13, wherein said pyruvate carboxylase is from *Lactobacillus lactis* or *Sorghum vulgare* or *Rhizobium etli*.

15. The nonnaturally occurring *Escherichia coli* bacterium of claim 13 further comprising a mutation in a gene that causes an increased level of phosphoenolpyruvate carboxykinase activity.

16. The nonnaturally occurring microbial strain *Escherichia coli* bacterium of claim 15, wherein the increased level of phosphoenolpyruvate carboxykinase activity results from a mutation in a pck gene.

17. The nonnaturally occurring *Escherichia coli* bacterium of claim 15, wherein said mutation in pck gene is in the region of said pck gene that is upstream from the coding region.

18. The nonnaturally occurring *Escherichia coli* bacterium of claim 15, wherein the increase in the level of phosphoenolpyruvate carboxykinase activity results from replacement of the native promoter sequence of pck gene with an exogenous promoter sequence.

19. The nonnaturally occurring *Escherichia coli* bacterium of claim 5, wherein said non-PTS sugar transporter is a facilitated diffuser.

* * * * *